US012569276B2

(12) United States Patent
Lagasse et al.

(10) Patent No.: US 12,569,276 B2
(45) Date of Patent: Mar. 10, 2026

(54) MINIMALLY INVASIVE CELL TRANSPLANT PROCEDURE TO INDUCE THE DEVELOPMENT OF IN VIVO ORGANOGENESIS

(71) Applicant: UNIVERSITY OF PITTSBURGH—OF THE COMMONWEALTH SYSTEM OF HIGHER EDUCATION, Pittsburgh, PA (US)

(72) Inventors: Eric Lagasse, Pittsburgh, PA (US); Paulo Artur Chaves Fontes, Pittsburgh, PA (US)

(73) Assignee: UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 906 days.

(21) Appl. No.: 17/498,168

(22) Filed: Oct. 11, 2021

(65) Prior Publication Data

US 2022/0096126 A1      Mar. 31, 2022

Related U.S. Application Data

(63) Continuation of application No. PCT/US2020/027783, filed on Apr. 10, 2020.

(60) Provisional application No. 62/832,492, filed on Apr. 11, 2019.

(51) Int. Cl.
| | |
|---|---|
| A61B 17/34 | (2006.01) |
| A61L 27/38 | (2006.01) |
| A61B 17/00 | (2006.01) |

(52) U.S. Cl.
CPC ...... A61B 17/3468 (2013.01); A61B 17/3403 (2013.01); A61L 27/3804 (2013.01); A61L 27/3839 (2013.01); A61B 2017/00969 (2013.01); A61B 2017/3413 (2013.01)

(58) Field of Classification Search
None
See application file for complete search history.

(56) References Cited

U.S. PATENT DOCUMENTS

| | | | |
|---|---|---|---|
| 6,610,288 | B1 | 8/2003 | Edge et al. |
| 9,125,891 | B2 | 9/2015 | Lagasse |
| 9,533,013 | B2 | 1/2017 | Reid et al. |
| 2004/0110289 | A1 | 6/2004 | Ludlow et al. |
| 2006/0106306 | A1 | 5/2006 | Essner et al. |
| 2007/0237373 | A1 | 10/2007 | Kiraly et al. |
| 2011/0002899 | A1 | 1/2011 | Lagasse |
| 2012/0045764 | A1 | 2/2012 | Grompe et al. |
| 2015/0213731 | A1 | 7/2015 | Sato et al. |

| | | | |
|---|---|---|---|
| 2016/0058794 | A1 | 3/2016 | Lagasse |
| 2016/0058798 | A1 | 3/2016 | Reid et al. |
| 2016/0199416 | A1 | 7/2016 | Lee et al. |
| 2017/0071504 | A1 | 3/2017 | Wang |
| 2019/0099198 | A1* | 4/2019 | Snoke .................. A61M 5/178 |

FOREIGN PATENT DOCUMENTS

| | | |
|---|---|---|
| CN | 202761247 U | 3/2013 |
| EP | 1 829 571 A1 | 9/2007 |
| JP | 2000-107299 A | 4/2000 |
| JP | 2015-145354 A | 8/2015 |
| WO | WO 1998/009247 A1 | 3/1998 |
| WO | WO 2014/138486 A1 | 9/2014 |
| WO | WO 2014/182885 A2 | 11/2014 |
| WO | WO 2018/134729 A1 | 7/2018 |
| WO | WO 2018/152488 A1 | 8/2018 |
| WO | WO 2018/222724 A1 | 12/2018 |
| WO | WO 2018/227101 A1 | 12/2018 |
| WO | WO 2019/006127 A1 | 1/2019 |

OTHER PUBLICATIONS

Tantawy, et al. (2011) "Extrapleural paravertebral CT guided fine needle biopsy of subcarinal lymph nodes", European Journal of Radiology, 81: 2907-19. (Year: 2011).*

Kancharla, et al. (2010) "Transitional Cell Carcinoma of the Bladder Manifestating as Malignant Lymphomoa with Generalized Lymphadenopathy", Case Reports in Oncology, 3(2): 125-30. (Year: 2010).*

Pratt, et al. (1975) "Mesocolic lymph node histology is an important prognostic indicator for patients with carcinoma of the sigmoid colon: an immunomorphologic study", Cancer, 35(5): 1388-96 (Abstract Only)). (Year: 1975).*

Reddy and Willert (2009) "Endoscopic Ultrasound: what is it and when should it be used", Clinical Medicine, 9(6): 539-43. (Year: 2009).*

Komori et al., "The mouse lymph node as an ectopic transplantation site for multiple tissues," Nature Biotechnology, 30(10):976-983 (2012).

Supplementary European Search Report dated Nov. 25, 2022 in Application No. EP 20788083.

International Search Report and Written Opinion dated Jul. 6, 2020 in International Application No. PCT/US2020/027783.

Kam et al., "Evidence that Host Size Determines Liver Size: Studied in Dogs Receiving Orthotopic Liver Transplants," 362-366 (1987).

Li et al., "The spleen in liver cirrhosis: revisiting an old enemy with novel targets." Journal of Translational Medicine 15:111 1-10 (2017).

Seglen, "Chapter 4 Preparation of Isolated Rat Liver Cells," Methods Cell Biol, 13, 29-83 (1976).

Sohlenius-Sternbeck, "Determination of the hepatocellularity number for human, dog, rabbit, rat and mouse livers from protein concentration measurements," Toxicology in Vitro, 20(8), 1582-1586 (2006).

(Continued)

*Primary Examiner* — Robert M Kelly
(74) *Attorney, Agent, or Firm* — Baker Botts L.L.P.

(57) ABSTRACT

Provided herein are methods and systems of transplant cells and growing an ectopic tissue in a lymph node of a subject. In certain embodiments, the methods and systems provided herein enable minimally invasive cell transplantation to treat patients in need thereof. In certain embodiments, the methods and systems provided herein include the use of ultrasound endoscopy.

37 Claims, 10 Drawing Sheets

(56) References Cited

OTHER PUBLICATIONS

Soltys et al., "Barriers to the successful treatment of liver disease by hepatocyte transplantation." Journal of Hepatology 53(4): 769-774 (2010).

Irisawa et al., "Endoscopic ultrasound-guided immunotherapy," Gastrointest Interv 3:24-26 (2014).

Yan et al., "Endoscopic ultrasound-guided intratumoural therapy for pancreatic cancer," Can J Gastroenterol 22(4):405-410 (2008).

Ito et al., "Intrasplenic Hepatocyte Transplantation Prolonged the Survival in Nagase Analbuminemic Rats With Liver Failure Induced by Common Bile Duct Ligation," Cell Transplantation 16:547-553 (2007).

Bourdel et al., "Assessment of sentinel nodes for gynecologic malignancies by natural orifices transluminal endoscopic surgery (NOTES): Preliminary report," Gynecologic Oncology, 115(3):367-370 (2009).

Extended European Search Report dated Nov. 19, 2024, in Application No. EP 24174926.

Francipane et al., "Pluripotent Stem Cells to Rebuild a Kidney: The Lymph Node as a Possible Developmental Niche," Cell Transplantation, 25:1007-1023 (2016).

Korzeniowski et al., "NOViSE: a virtual natural orifice transluminal endoscopic surgery simulator," International Journal of Computer Assisted Radiology and Surgery, 11(12):2303-2315 (2016).

Ohdaira et al., "Ultra-minimally invasive local immune cell therapy and regenerative therapy by multi-piercing surgery for abdominal solid tumor: therapeutic simulation by natural orifice translumenal endoscopic surgery-assisted needlescopic surgery using 3-mm diameter robots," Journal of Hepato-Biliary-Pancreatic Sciences 18(4):499-505 (2011).

Tan to Sui (Journal of Biliary Tract & Pancreas), 2009, vol. 30 extra issue, pp. 1257-1261 [with English translation].

Chang et al., "Phase I Clinical Trial of Allogeneic Mixed Lymphocyte Culture (Cytoimplant) Delivered by Endoscopic Ultrasound2Guided Fine-Needle Injection in Patients with Advanced Pancreatic Carcinoma," Cancer, 88(6):1325-1335 (2000).

Irisawa et al., "W1219 Endoscopic Ultrasound-Guided Fine Needle Injection of Immature Dendritic Cells into Advanced Pancreatic Carcinoma Refractory to Gemcitabine: A Pilot Study," Gastrointestinal Endoscopy, 61(5):AB283 (2005).

Ohno et al., "Successful treatment against lymphnode metastasis by endoscopic ultrasonography-guided ethanol injection in a case of hepatocellular carcinoma," Kanzo 52(10):671-678 (2011) [with English abstract].

* cited by examiner

Normal Liver
(Animal #6303-1)    CK18 / Hoechst

HTs in LN via EUS Injection
(Animal #6303-3)

HTs in LN via Direct Injection
(Animal #6303-3)

MINIMALLY INVASIVE CELL TRANSPLANT PROCEDURE TO INDUCE THE DEVELOPMENT OF IN VIVO ORGANOGENESIS

PRIORITY CLAIM

This application is a continuation of International Patent Application No. PCT/US2020/027783, filed Apr. 10, 2020, which claims priority to U.S. Provisional Application Ser. No. 62/832,492 filed Apr. 11, 2019, the contents of each of which are hereby incorporated by reference in their entireties.

INTRODUCTION

The present disclosure relates to minimally invasive methods for transplanting cells into a lymph node of a subject to generate functional ectopic tissues and organs.

BACKGROUND

There is a great demand for organ transplant and/or regeneration. However, the shortage of organs available for transplant to terminally ill patients represents a major worldwide medical, social and economic challenge. In addition, whole organ transplantation can have stringent requirements as to the recipient's own health status. For instance, there are currently around 30,000 patients/year with end-stage liver disease (ESLD) in the US that do not qualify for standard liver transplantation.

An alternative approach to whole-organ transplant can involve the transplantation of cells to regenerate failing organs. For instance, hepatocyte transplantation (HT) can prolong and enhance the quality of life of patients with ESLD who would be considered unsuitable for standard liver transplantation and have no additional therapeutic option. However, orthotopic cell-based therapy directed at a diseased organ may not be feasible for many reasons, ranging from a possible lack of an appropriate environment in cirrhotic and fibrotic liver during end-stage disease to the lack of a thymus in complete DiGeorge syndrome.

For patients suffering from ESLD, there can be a significant challenge: most cellular therapies have been directed to promote cell engraftment into the native diseased liver. Transplanted liver cells are generally injected into the spleen (splenic artery in patients or splenic parenchyma in rodents) or intrahepatic via the portal vein. Liver cells transplanted into the splenic artery can rapidly migrate, actively or passively, to the diseased liver after the initial splenic injection, where hepatic regeneration by the transplanted hepatocytes is expected to occur. However, this approach has significant limitations because of the anatomical site of transplantation. Most of these patients with ESLD (Takahashi et al., 2014), have splenomegaly and hypersplenism, where aggressive cell trapping followed by phagocytosis and cell destruction can take place in the spleen regarding all cells (e.g., red blood cells, leukocytes and platelets) entering the splenic parenchyma through the splenic artery circulation. In addition, the transplanted hepatocytes can be further directed to the liver through the splenic vein as a major component of the portal vein supply into the liver parenchyma. These cells can circulate from the portal triads into the hepatic sinusoids where partial occlusion of small portal vein branches and hepatic sinusoids by hepatocytes leads to transient portal hypertension, initial ischemia and the death of many of the transplanted cells (da Fonseca et al., 2008).

The transplanted hepatocytes can have very limited ability to overcome the sinusoidal endothelial cell barrier and engraft within the hepatic parenchyma. Moreover, patients with ESLD can have significant degrees of hepatic fibrosis and cirrhosis, which can be major limiting factors for subsequent cell growth within the hepatic lobule already restricted by progressive cytoarchitecture disarray.

Thus, there remains a need for novel cell-based organ regeneration methods capable to generate functional organs with reasonable anatomic features. There also remains a need for novel treatments for ESLD, metabolic liver diseases and acute liver failure.

SUMMARY

In one aspect, the present disclosure provides a minimally invasive method of transplanting one or more cells and growing an ectopic tissue in a subject. In certain embodiments, the method comprises advancing an endoscope through an endoluminal approach, e.g., into the gastrointestinal, respiratory, or urinary tract of the subject, utilizing a transluminal approach to insert a needle attached to the endoscope through a visceral wall into a lymph node of the subject, and delivering one or more cells into the lymph node via the needle, thereby allowing the one or more cells to engraft and produce the ectopic tissue in the lymph node.

In certain embodiments, advancing the endoscope, inserting the needle, or both are performed with the aid of radiological imaging or ultrasound imaging. In certain embodiments, radiological imaging comprises dynamic radiological imaging, computed tomography (CT), magnetic resonance imaging (MRI) or both. In certain embodiments, the lymph node is in the abdominal or thoracic cavity of the subject. In certain embodiments, the lymph node is in the mediastinal or retroperitoneal region of the subject.

In certain embodiments, a minimally invasive method of transplanting one or more cells and growing an ectopic tissue in a subject of the present disclosure includes inserting a needle into lymph node(s) in the abdominal or thoracic cavity of the subject with the aid of ultrasound or radiological imaging, and delivering one or more cells into the lymph node via the needle, thereby allowing the one or more cells to engraft, expand and differentiate into an ectopic tissue in the lymph node. In certain embodiments, the method further comprises advancing an endoscope through the gastrointestinal, respiratory, or urinary tract of the subject, and utilizing a transluminal approach to insert the needle through a visceral wall to reach the lymph node of the subject, wherein the needle is attached to the endoscope. In certain embodiments, advancing the endoscope, inserting the needle or both are performed with the aid of ultrasound imaging of the lymph node. In certain embodiments, the radiological imaging comprises dynamic radiological imaging, computed tomography (CT), magnetic resonance imaging (MRI) or both. In certain embodiments, the endoscope comprises an ultrasound probe configured to detect the lymph node.

In certain embodiments, the one or more cells comprise hepatocytes, pancreatic cells or islets, kidney cells or fragments, thymic cells or fragments, or lung cells or fragments. In certain embodiments, the one or more cells are autologous, allogenic, or xenogeneic to the subject. In certain embodiments, the one or more cells are syngeneic to the subject.

In certain embodiments, the methods disclosed herein further comprises isolating the one or more cells from a live donor tissue. In certain embodiments, the methods disclosed herein further comprises recovering the one or more cells from cryopreservation prior to the delivering. In certain embodiments, the method further comprises administering an immunosuppressant to the subject to reduce immune rejection of the one or more cells.

In certain embodiments, the method comprises delivering the one or more cells into at least 2, 3, 4, 5, 6, 7, 8, 9, 10, or more lymph nodes in the abdominal or thoracic cavity.

In certain embodiments, the one or more cells comprise cells of an average diameter of about 20 μm. In certain embodiments, the one or more cells comprise at least about 10 million, 20 million, 30 million, 40 million, 50 million, 60 million, 70 million, 80 million, 90 million, or 100 million cells per delivery into one single lymph node. In certain embodiments, the needle delivers the one or more cells in a suspension solution that has at least about 10 million, 20 million, 25 million, 30 million, 40 million, 45 million, 50 million, 55 million, 60 million, 70 million, 80 million, 90 million, or 100 million cells per mL. In certain embodiments, the needle delivers the one or more cells in a suspension solution that has at least about 10 million, 20 million, 30 million, 40 million, or 50 million viable cells per mL. In certain embodiments, the one or more cells are delivered into the lymph node in a population of cells, and wherein the population of cells has at least about 50%, 55%, 60%, 65%, 66%, 67%, 68%, 69%, 70%, 71%, 72%, 73%, 74%, 75%, 80%, 85%, 90%, 95%, or about 100% viable cells. In certain embodiments, the one or more cells are delivered into the lymph node in a population of cells, and wherein the delivering leads to less than about 20%, 15%, 10%, 9%, 8.5%, 8%, 7.5%, 7%, 6.5%, 6%, 5.5%, 5%, 4.5%, 4%, 3.5%, 3%, 2.5%, 2%, 1.5%, 1%, or 0.5% reduction in cell viability percentage in the population of cells when the one or more cells pass through the needle.

In certain embodiments, an inner diameter of the needle is at most about 700 μm, 600 μm, 500 μm, 450 μm, 400 μm, 300 μm, 260 μm, 250 μm, or 200 μm. In certain embodiments, an inner diameter of the needle is at most about 260 μm. In certain embodiments, an outer diameter of the needle is at most about 1 mm, 900 μm, 800 μm, 750 μm, 700 μm, 650 μm, 600 μm, 550 μm, 520 μm, 510 μm, 500 μm, 480 μm, 450 μm, or 400 μm. In certain embodiments, an outer diameter of the needle is at most about 510 μm. In certain embodiments, the needle is at most about 19, 19.5, 20, 20.5, 21, 21.5, 22, 22.5, 23.5, 24, 24.5, 25, 25.5, 26, 26.5, or 27 gauge. In certain embodiments, the needle is at most about 25 gauge. In certain embodiments, the needle is at most about 25 gauge, and the needle delivers the one or more cells in a suspension solution that has at least about 50 million viable cells per mL, and wherein the one or more cells comprise at least about 65% viable cells.

In certain embodiments, the one or more cells comprise hepatocytes and the ectopic tissue is ectopic liver tissue. In certain embodiments, the method treats a liver disease or condition in the subject. In certain embodiments, the liver disease or condition is end stage liver disease or liver fibrosis related to alcohol consumption, Hepatitis A, B, C or D infection, nonalcoholic fatty liver disease, autoimmune hepatitis, primary biliary cirrhosis, primary sclerosing cholangitis, biliary atresia, cystic fibrosis, Alagille syndrome, syphilis, brucellosis, parasitic infections, chemical exposure, chronic biliary diseases, Budd-Chiary Syndrome, Osler Disease, or right heart failure. In certain embodiments, the liver disease or condition is associated with a metabolic disorder comprising tyrosinemia, maple syrup urine disease, phenylketonuria, Crigler-Najjar syndrome, oxalosis, hyperoxaluria, hemochromatosis, Alpha-1 antitrypsin deficiency, Wilson disease, familial intrahepatic cholestasis syndromes, galactosemia, glycogen storage disease, or familial amyloid polyneuropathy. In certain embodiments, the subject has received a portacaval shunt surgical procedure or Transjugular Intrahepatic Portosystemic Shunt (TIPS) that reduces blood supply to liver of the subject and induces hepatocellular dysfunction in the subject, and wherein the portacaval shunt surgical procedure comprises end-to-side portacaval shunt, side-to-side portacaval shunt, mesocaval shunt with interposition H- or C-grafts, or central or distal splenorenal shunt. In certain embodiments, the method treats end-stage liver disease in the subject.

In certain embodiments, the one or more cells comprise kidney cells or kidney fragments and the ectopic tissue is ectopic kidney tissue. In certain embodiments, the method treats a renal disease or condition in the subject. In certain embodiments, the renal disease or condition is an end stage renal disease.

In certain embodiments, the one or more cells comprise pancreatic cells or islets and the ectopic tissue is ectopic pancreatic tissue. In certain embodiments, the method treats an endocrine pancreatic disease or condition that leads to reduction or absence of insulin secretion in the subject. In certain embodiments, the pancreatic disease or condition is type I diabetes, type II diabetes, or chronic pancreatitis that leads to reduction of insulin secretion in the subject.

In certain embodiments, the one or more cells comprise lung cells or lung fragments and the ectopic tissue is ectopic lung tissue. In certain embodiments, the method treats a lung disease or condition in the subject. In certain embodiments, the lung disease or condition is chronic obstructive pulmonary disease (COPD). In certain embodiments, the COPD is caused by: cigarette smoke, pollutions and fumes, alpha-1-antiytrypsin, cystic fibrosis, chronic asthma, emphysema, chronic bronchitis, or idiopathic pulmonary fibrosis.

In certain embodiments, the one or more cells comprise thymic cells or thymus fragments, and the ectopic tissue is ectopic thymus tissue. In certain embodiments, the thymic cells or fragments are obtained from a donor subject and the ectopic thymus tissue induces donor-specific tolerance in the subject to transplantation of cells from the donor subject. In certain embodiments, the disease or condition is age-related immune system malfunction, and the ectopic thymus tissue modulates immune function of the subject.

In certain embodiments, the lymph node is in proximity to the gastrointestinal tract, and the endoscope is advanced along the gastrointestinal tract. In certain embodiments, the lymph node comprises one or more of a periduodenal lymph node, a perigastric lymph node, a peripancreatic lymph node, a mesenteric lymph node, an ileocolic lymph node, a mesocolic lymph node, a gastric lymph node, a hepatic splenic lymph node, a splenic hilar lymph node, a paraoesophageal lymph node, a paracardial lymph node, a paraaortic lymph node, a retroaortic lymph node, a lateral aortic lymph node, a preaortic lymph node, a lesser curve lymph node, a common hepatic lymph node, a splenic artery lymph node, a coeliac axis lymph node, an iliac lymph node, or a retroperitoneal lymph node. In certain embodiments, the lymph node comprises a periduodenal lymph node. In certain embodiments, the lymph node is in proximity to the respiratory tract, and the endoscope is advanced along the respiratory tract. In certain embodiments, the lymph node comprises one or more lymph nodes in mediastinal region. In certain embodiments, the lymph node comprises one or more of a parasternal lymph node, an intercostal lymph node, a superior diaphragmatic lymph node, a superior tracheobronchi lymph node, an inferior tracheobronchi lymph node, a bronchopulmonary lymph node, a paratracheal lymph node, or an intrapumonary lymph node. In certain embodiments, the lymph node is in proximity to the urinary tract and the endoscope is advanced along the urinary tract. In certain embodiments, the lymph node comprises one or more lymph nodes in retroperitoneal region. In certain embodiments, the lymph node comprises one or more of an external iliac lymph node, an internal iliac lymph node, a caval lumbar lymph node, an aortic lumbar lymph node, a superficial inguinal lymph node, a profound inguinal lymph node, an interaortocaval peri-bladder lymph node, an obturator peri-bladder lymph node, or a pre-sacral peri-bladder lymph node.

In certain embodiments, the subject is a human. In certain embodiments, the subject is a non-human animal.

In certain embodiments, the ectopic tissue is formed within about 5 days, 10 days, 15 days, 20 days, 25 days, 30 days, 35 days, 40 days, 45 days, 50 days, 55 days, 60 days, 65 days, 70 days, 75 days, 80 days, 85 days, 90 days, 95 days, 100 days, 110 days, 120 days, 130 days, 140 days, 150 days, 160 days, 170 days, 180 days, 190 days, or about 200 days after delivering the one of more cells into a lymph node.

The present disclosure further provides a method of treating a liver disease in a subject in need thereof. In certain embodiments, the method comprises advancing an endoscope through an endoluminal approach into the gastrointestinal, respiratory, or urinary tract of the subject, utilizing a transluminal approach to insert a needle attached to the endoscope through a visceral wall into a lymph node of the subject with the aid of ultrasound imaging, and delivering the one or more cells into the lymph node via the needle, thereby allowing the one or more cells to engraft and produce an ectopic liver tissue in the lymph node. In non-limiting embodiments, the ectopic tissue is formed within about 5 days, 10 days, 15 days, 20 days, 25 days, 30 days, 35 days, 40 days, 45 days, 50 days, 55 days, 60 days, 65 days, 70 days, 75 days, 80 days, 85 days, 90 days, 95 days, 100 days, 110 days, 120 days, 130 days, 140 days, 150 days, 160 days, 170 days, 180 days, 190 days, or about 200 days after delivering the one of more cells into a lymph node.

The present disclosure provides a system for transplanting hepatocytes and growing an ectopic liver in a subject, comprising an endoscope and an injector having a needle and a population of cells in a suspension solution contained therein, wherein the suspension solution has from about 25 million to about 100 million viable hepatocytes per mL, and wherein the needle is at most about 25 gauge. In certain embodiments, the endoscope and the needle are configured to advance together along gastrointestinal, respiratory, or urinary tract of the subject. In certain embodiments, the injector is configured to deliver the one or more cells via the needle. In certain embodiments, the endoscope comprises an ultrasound probe. In certain embodiments, the ultrasound probe is configured to detect a lymph node in abdominal cavity of the subject. In certain embodiments, the suspension solution has at least about 30 million, 40 million, 45 million, 50 million, 55 million, 60 million, 70 million, 80 million, 90 million, or 100 million cells per mL. In certain embodiments, the population of cells in the injector has at least about 50%, 55%, 60%, 65%, 66%, 67%, 68%, 69%, 70%, 71%, 72%, 73%, 74%, 75%, 80%, 85%, 90%, 95%, or about 100% viable cells. In certain embodiments, the population of cells in the injector has at least about 65% viable cells. In certain embodiments, the population of cells in the injector comprises at least about 10 million, 20 million, 30 million, 40 million, 50 million, 60 million, 70 million, 80 million, 90 million, or 100 million cells. In certain embodiments, the population of cells in the injector comprises at least about 50 million viable cells per mL, and the population of cells comprise at least about 65% viable cells.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1A:
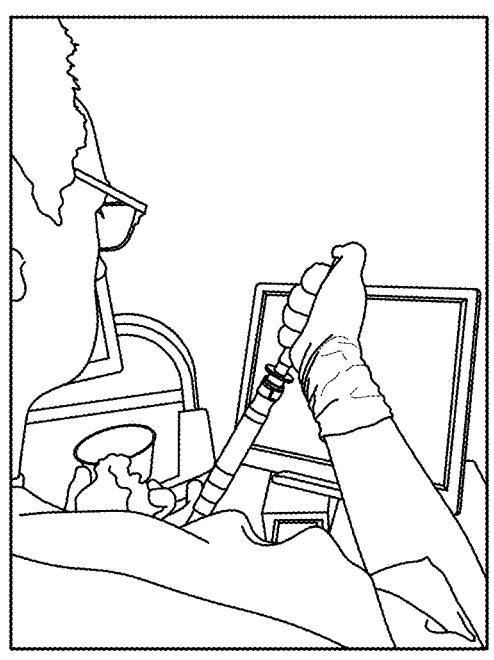
FIG. 1A is a picture of an endoscopist conducting ultrasound endoscopy on an experimental animal for EUS-guided cell delivery into lymph node.

For clarity, but not by way of limitation, the detailed description of the presently disclosed subject matter is divided into the following subsections:

1. Overview;
2. Definitions;
3. Cell Delivery Procedures;
4. Production of Ectopic Tissue from Transplanted Cells;
5. Diseases and Conditions;
6. Subjects;
7. Systems; and
8. Kits.

1. Overview

As an overview, the present disclosure relates to methods and systems for minimally invasive procedures to induce the development of in vivo organogenesis. Provided herein are methods and systems for transplanting cells and growing an ectopic tissue in a subject by delivering cells into a lymph node of the subject. The process of growing the ectopic tissue from the delivered cells or tissue fragments inside the lymph node with proper anatomical and functional features is termed in vivo organogenesis. The minimally invasive procedures enabled by the present disclosure can lead to production of ectopic tissue(s) that can supplement or augment normal function of one or more organs for the subject.

As discussed above, one problem associated with current transplantation therapies, particularly orthotopic organ transplant, can be that many patients with end-stage diseases, such as end-stage liver or renal diseases, are no longer suitable for major surgeries that can be required for orthotopic organ transplant or other types of cells transplant. There can be significant risks associated with the major surgeries and the prognostication in these patients can be poor given their deteriorated health conditions. In one aspect, the present disclosure provides a minimally invasive procedure (e.g., endoscopic ultrasound (EUS)) to solve this problem. The methods and systems can generate anatomically intact and fully or at least partially functional organs in ectopic sites using the lymph node as natural bioreactors. The methods and systems provided herein can minimize the morbidity and the mortality for patients with end organ disease that can be often associated with additional surgical procedures. The present disclosure can also allow at least some of the surgical procedures described herein to be conducted on an outpatient basis, therefore can decrease the costs of the initial procedure.

As used herein, the term "ectopic tissue" can refer to a tissue existing at an ectopic (non-native) location of a body and having one or more morphological and/or functional properties similar to or same as a healthy organ or tissue that can normally be found at a native location of the body. The term "functional ectopic tissue" can refer to an ectopic tissue that has one or more of the functions of a healthy organ or tissue that can normally be found at a native location of the body. The term "ectopic location" can be used to describe a location relative to a native location of the subject, e.g., an ectopic location can refer to a location that is different than the native location in the subject's body. For instance, a liver in a lymph node is ectopic, i.e., an ectopic liver, in a healthy normal mammalian body because liver tissue is typically not found in a lymph node. According to some aspects of the present disclosure, ectopic tissue can grow in a lymph node that contains a population of cells that morphologically resemble hepatocytes and collectively can perform one or more functions that a healthy native liver can perform.

In certain embodiments, the methods include advancing an endoscope into a body lumen or a closed body cavity of a subject. In certain embodiments, the methods include advancing an endoscope into the gastrointestinal (GI), respiratory, or urinary tract of the subject.

In certain embodiments, the endoscope is advanced into a body lumen of the subject through an endoluminal approach. As used herein the term "endoluminal approach" as used herein refers any approaches, e.g., methods and devices, known in the art for inserting an endoscope into a body lumen of the subject. For example, but not by way of limitation, the methods include advancing an endoscope through an endoluminal approach into the gastrointestinal (GI), respiratory, or urinary tract of the subject.

In certain embodiments, the methods can further include inserting a needle into a lymph node of the subject, where the needle is attached to the endoscope. In certain embodiments, the needle attached to the endoscope is inserted through a visceral wall into a lymph node. Non-limiting examples of visceral walls include anatomical structures enclosing a hollow viscera and/or an organ along the tract, for instance, stomach, duodenum, trachea, bronchi, or bladder. In certain embodiments, the methods further include inserting the needle through a transluminal approach. As used herein, the term "transluminal approach" refers to any approaches, e.g., methods and devices, known in the art for inserting a working instrument (e.g., a needle) across a lumen via the use of an endoscope.

In certain embodiments, the methods further include delivering one or more cells into the lymph node via the needle. In certain embodiments, the methods include delivering one single cell into the lymph node. In certain embodiments, the methods include delivering a population of cells into the lymph node. In certain embodiments, the population of cells includes one cell type. In certain embodiments, the population of cells includes at least two cell types. In certain embodiments, the one or more cells delivered into the lymph node can engraft and produce the ectopic tissue in the lymph node.

In certain embodiments, advancing the endoscope, inserting the needle, or both are performed by a minimally invasive or non-invasive method. For example, ultrasound-mediated imaging or other detection methods can be applied in the methods provided herein for location of the target lymph node. During the process, ultrasound imaging or other methods, e.g., minimally invasive or noninvasive detection approaches, can be applied for any of advancing the endoscope, locating the suitable target lymph node, or monitoring the insertion of the needle through the visceral wall or into the target lymph node.

In another aspect, the present disclosure provides methods that include inserting a needle into a lymph node in the abdominal, pelvis or thoracic cavity of the subject with the aid of ultrasound. The methods can further include delivering one or more cells into the lymph node via a needle. Ultrasound-guided location of a lymph node can be performed by any technology available. For example, but not by way of limitation, one can use ultrasound imaging to identify and locate a suitable lymph node for injection of the cells. In certain embodiments, ultrasound spectrometry can be utilized for detecting the lymph node. In certain embodiments, ultrasound imaging or spectrometry can be used in conjunction with other detection methods for localization of the lymph node.

In certain embodiments, the methods include delivering a population of cells into a lymph node of the subject, where the population of hepatocytes engrafts and produces an ectopic liver in the lymph node. In certain embodiments, the methods further include reducing blood supply to the liver of the subject. It has been discovered by the present disclosure that a reduction in the blood supply to the liver of the subject benefits the growth of the ectopic liver in the lymph node.

2. Definitions

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C." The term "or" can be used conjunctively or disjunctively, unless the context specifically refers to a disjunctive use. Furthermore, use of the term "including" as well as other forms, such as "include", "includes," and "included," is not limiting.

Reference in the specification to "some embodiments," "certain embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the present disclosure, and vice versa. Furthermore, compositions of the present disclosure can be used to achieve methods of the present disclosure.

The term "about" in relation to a reference numerical value and its grammatical equivalents as used herein can include the numerical value itself and a range of values plus or minus 10% from that numerical value.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

3. Cell Delivery Procedures

In certain embodiments, methods and systems of the present disclosure make use of an endoscope for transluminal delivery of cells into a lymph node of a subject. In certain embodiments, the lymph node is located in proximity to or within a body lumen or a closed body cavity that can be reached through the use of the endoscope. In certain embodiments, the lymph node is located in the abdominal, pelvis or thoracic cavity of a subject.

As used herein, the term "endoscope" can refer to any instrument that can be introduced into the body of a subject, e.g., a human subject or a non-human mammalian subject, e.g., dog, pig, horse, donkey, rabbit, ox, mouse, or rat, and provide a view of the internal parts of the subject. Sometimes, the view provides visual inspection, for instance, when the endoscope is equipped with illuminated optics or otherwise aided with illumination. In certain embodiments, an endoscope of the present disclosure includes or is attached to or associated with one or more detection probes and offer different detection modes for examination of the internal parts of the subject. For instance, the endoscope can have illuminated optics for visual inspection, ultrasound probe for ultrasound-mediated detection (e.g., ultrasound imaging), or detectors for radiation, infrared signal, radiofrequency signal, or fluorescence signal.

An endoscope described herein can include one or more of the following parts: a rigid or flexible tube to travel along the luminal tract of the subject (e.g., GI tract, respiratory tract, or urinary tract); a light delivery system to illuminate the organ or object under inspection; a lens system transmitting the image from the objective lens to a viewer, an eyepiece or a video system that displays the images captured by the endoscope inside the body; one or more channels to allow entry of medical instruments or manipulators. The light source can be outside the body or of a mini size and equipped inside the endoscope. When the light source is outside the body, the light can be transmitted via an optical fiber system. There can be an optic system, e.g., fiber optics, for transmitting the light images captured inside the body. Additionally or alternatively, an endoscope provided herein can be equipped with (e.g., include as a part or attached to) other detection instrument for different purposes.

The methods provided herein can include advancing the endoscope in a body lumen or a closed body cavity of a subject. Non-limiting examples of body lumens include gastrointestinal (GI) tract (e.g., esophagus, stomach, duodenum, small intestine, large intestine, colon, bile duct, rectum, anus), respiratory tract (e.g., nose, lower respiratory tract), ear, urinary tract, cervix, uterus, and fallopian tube. Non-limiting examples of closed body cavities include abdominal cavity, and pelvic cavity. In certain embodiments, the methods disclosed herein include advancing the endoscope in the gastrointestinal, respiratory, or urinary tract of the subject.

In certain embodiments, the methods disclosed herein include advancing the endoscope along a body lumen or in a closed body cavity of a subject for delivering cells into at least one lymph node that is located in proximity to or in the body lumen or the closed body cavity. In certain embodiments, the location of the lymph node is chosen based on the purpose of the cell transplantation. In certain embodiments, the lumen and/or closed body cavity is chosen based on the lymph node that is suitable for cell transplantation.

In certain embodiments, the methods disclosed herein includes advancing the endoscope along the GI tract for delivering cells into one or more lymph nodes in proximity to the GI tract. An endoscope (e.g., an esophagoscope or a gastroscope) can be used to deliver cells into lymph nodes in proximity to the upper part or lower part of the GI tract. For instance, an esophagoscope can be used to deliver cells into lymph nodes close to the esophagus, and a gastroscope can be used to deliver cells into the perigastric and/or periduodenal lymph nodes. Non-limiting examples of lymph nodes in proximity to the GI tract in which cells can be delivered into using the methods provided herein include periduodenal lymph node, perigastric lymph node, peripancreatic lymph node, mesenteric lymph node, ileocolic lymph node, mesocolic lymph node, gastric lymph node, hepatic splenic lymph node, splenic hilar lymph node, paraoesophageal lymph node, paracardial lymph node, paraaortic lymph node, retroaortic lymph node, lateral aortic lymph node, preaortic lymph node, lesser curve lymph node, common hepatic lymph node, splenic artery lymph node, coeliac axis lymph node, iliac lymph node, and retroperitoneal lymph node. The endoscope can be introduced from the mouth of the subject, or in certain embodiments, from the nose of the subject. Alternatively, the endoscope can be introduced from the anus of the subject, for instance, a proctoscope, sigmoidoscope, or colonoscope can be used to deliver cells into lymph nodes close to rectum or colon. In certain embodiments, the endoscope is flexible to travel along the GI tract, and an investigative examination is conducted in order to locate the suitable lymph node for the purpose of cell transplantation.

In certain embodiments, the methods disclosed herein include advancing the endoscope along the respiratory tract of the subject for delivering cells into one or more lymph nodes in proximity to the respiratory tract. For example, but not by way of limitation, a bronchoscope or a laryngoscope is used to target lymph nodes close to trachea or bronchi of the lungs, or the larynx of the subject. Non-limiting examples of lymph nodes in proximity to the respiratory tract in which cells can be delivered into using methods provided herein include parasternal lymph node, an intercostal lymph node, superior diaphragmatic lymph node, superior tracheobronchi lymph node, inferior tracheobronchi lymph node, bronchopulmonary lymph node, paratracheal lymph node, and intrapumonary lymph node. The bronchoscope or laryngoscope can be introduced from the mouth of the subject, or in certain embodiments, from the nose of the subject.

In certain embodiments, the methods disclosed herein includes advancing the endoscope along the urinary tract of the subject for delivering cells into one or more lymph modes in proximity to the urinary tract. For example, but not by way of limitation, a cystoscope is used to target lymph nodes close to urethra or bladder. The cystoscope can be introduced from the urethra of the subject. Non-limiting examples of lymph nodes in proximity to the urinary tract in which cells can be delivered into using methods provided herein include one or more of an external iliac lymph node, an internal iliac lymph node, a caval lumbar lymph node, an aortic lumbar lymph node, a superficial inguinal lymph node, a profound inguinal lymph node, an interaortocaval peri-bladder lymph node, an obturator peri-bladder lymph node, or a pre-sacral peri-bladder lymph node.

In certain embodiments, the methods disclosed herein include advancing the endoscope in a closed body cavity (e.g., abdominal cavity, pelvis cavity) for delivering cells into at least one lymph node inside or near the closed body cavity. In certain embodiments, the endoscope is introduced into the closed body cavity through a small incision, e.g., a small incision on the surface of the abdomen. In certain embodiments, the closed body cavity is an abdominal cavity or a pelvis cavity. Non-limiting examples of lymph nodes inside or near the abdominal cavity or pelvis cavity include splenic lymph nodes, hepatic lymph nodes, cystic lymph nodes, foraminal lymph nodes, right/left gastric lymph nodes, pyloric lymph nodes, super pyloric lymph nodes, sub pyloric lymph nodes, retro pyloric lymph nodes, superior pancreatic lymph nodes, inferior lymph nodes, superior/inferior pancreaticoduodenal lymph nodes, inferior mesenteric lymph nodes, sigmoid lymph nodes, superior rectal lymph nodes, mesocolic lymph nodes, left colic lymph nodes, right colic lymph nodes, middle colic lymph nodes, appendicular lymph nodes, ileocolic lymph nodes, retrocaecal lymph nodes, pretectal lymph nodes, superior mesenteric lymph nodes, left lumbar lymph nodes, lateral aortic lymph nodes, and preaortic lymph nodes.

In certain embodiments, the methods and systems disclosed herein use ultrasound for locating a lymph node in which cells will be transplanted, and/or for guiding the steps of advancing the endoscope through the body lumen or closed body cavity, inserting the needle, or any combination thereof. Ultrasound is sound waves with frequencies higher than the upper audible limit of human hearing, which can be about more than 20 kHz to several gigahertz. Ultrasound imaging (or sonography) can be performed in a variety of fashions depending on the intended purpose of applying the methods and systems provided herein. Non-limiting examples of sonography can include Doppler ultrasonography, contrast ultrasonography, molecular ultrasonography, elastography, interventional ultrasonography, and compression ultrasonography. In certain embodiments, the ultrasound imaging technology used herein has high spatial and/or temporal resolution for the purpose of locating the suitable lymph node for injection, using technologies such as those described in International Patent Publication Nos. WO2018222724A1 and WO2018134729A1, each of which is incorporated herein by reference.

In certain embodiments of the present disclosure, the methods disclosed herein uses endoscopy in combination with ultrasound imaging, where the endoscope is attached to an ultrasound probe (e.g., as part of the endoscope or as a separate piece). The term "ultrasound endoscopy," "endoscopic ultrasound," or "EUS," used interchangeably herein, can refer to a medical procedure in which endoscopy is combined with ultrasound to detect (e.g., to obtain images of), and/or manipulate the internal organs in the chest, abdomen and pelvis, or any other internal structures of a body. EUS instrument and technology used in the methods and systems provided herein can be those commercially available currently, and/or those as described in U.S. Patent Publication Nos. US20060106306A1 and US20070237373A1, and International Patent Publication No. WO1998009247A1, each of which is incorporated herein in its entirety by reference.

In certain embodiments, ultrasound imaging of the target lymph node (e.g., the lymph node into which one or more cells are to be delivered) is conducted with the aid of other imaging technologies, such as radiological imaging. Radiological imaging can include dynamic radiological imaging (fluoroscopy), computed tomography (CT), or magnetic resonance imaging (MRI). For example, but not by way of limitation, computed tomography (CT) is performed in order to gain anatomical information of the whole body or some local organ(s) or tissue(s) of the subject. In certain embodiments, magnetic resonance or any other medical arts available is used in conjunction with or in lieu of the ultrasound imaging for locating the target lymph node in the abdominal, pelvis or thoracic cavity of the subject.

The methods and systems provided herein can include using a needle for delivering the one or more cells into a lymph node. The needle can be part of an injector, which can be configured to receive the cells to be delivered and push the cells out through the needle for delivery. The needle provided herein can be configured to have certain a degree of sharpness and stiffness. For instance, the needle is to be inserted into the lymph node. In certain embodiments, the needle is also configured to penetrate the wall of the GI tract (e.g., the wall of esophagus, stomach, intestine, or colon), the respiratory tract, the urinary tract (e.g., the wall of the urethra or the bladder), so that the needle can reach the lymph node outside the tract. Any suitable needles known in the art can be used with the methods disclosed herein.

In certain embodiments, the needle is attached to the endoscope, e.g., as a part of the endoscope or as a separate instrument. The needle can be those used in Fine Needle Aspiration (FNA) procedures. FNA needles can be commercially available or specifically designed for the purpose of applying the teachings of the present disclosure. FNA needles are typically used for biopsy purpose, e.g., making cut into tissue and aspirating the tissue fragment for diagnostic purposes. In the methods and systems provided herein, FNA needles can be used for cell delivery purpose instead. In certain embodiments, the FNA needle is operated through a linear array echoendoscope EUS/FNA equipment. An exemplary EUS/FNA equipment can be configured for the controlled and measured advancement of the FNA needle (e.g., a hollow needle with a solid removable stylet) within a semirigid protective sheath. The EUS/FNA equipment can also have a handle with a port for stylet insertion or withdrawal and for attachment of a syringe from where live cells can be inserted. In certain embodiments, the needle is inserted within the protective sheath into the lymph node identified acoustically with the EUS probe from the echoendoscope equipment. The needle can then be advanced out of the sheath and inserted transluminally into the target lymph node under direct ultrasound guidance. A stopcock attached to the tip of the syringe can assist in creating and holding vacuum within the needle body. Once the needle tip is in the target lymph node and the stylet is removed, a syringe containing live cells in a culture medium can be connected onto the needle handle. Once the stopcock is opened, the needle placed within the lymph node parenchyma allows the cells to be infused promptly and under direct view. The needles can have adjustable spacers/sliders at the distal portion of the handle to allow modification of the length of sheath exiting the scope, which can assure an additional level of safety and accuracy when injecting nearby lymph nodes.

In certain embodiments, the needle is configured, e.g., the size of the needle is configured, for ease of injection of cells into the lymph node. In certain embodiments, the size (e.g., the gauge) of the needle is selected based on the location of the target lymph node, the type of cells to be delivered, and the amount of cells to be delivered. In certain embodiments, the smaller the needle is, the more flexible it is to reach and insert into a target lymph node. In certain embodiments, it is easier to insert a relatively small needle into a small target lymph node, which can otherwise tent around a relatively large needle. In certain embodiments, the size of the needle, e.g., the inner diameter of the needle, is configured to allow the cells being pushed out without clogging up the needle.

As described herein, the size of the needle refers to the size of the tip of the needle, not the hub of the needle where the needle is joined with other part of the injector. As disclosed herein, the outer diameter of the needle, refers to the first full diameter outside the wall of the needle from the tip, and the inner diameter of the needle refers to the first full diameter inside the wall of the needle from the tip.

In certain embodiments, the needle has an inner diameter of at most about 700 μm, 600 μm, 500 μm, 450 μm, 400 μm, 300 μm, 260 μm, 250 μm or 200 μm. In certain embodiments, the needle has an inner diameter of at most about 260 μm. In certain embodiments, the inner diameter of the needle can be about 700 μm, 600 μm, 500 μm, 450 μm, 400 μm, 300 μm, 260 μm, 250 μm, or 200 μm. In certain embodiments, the inner diameter of the needle is about 260 μm. The needle can have an outer diameter of at most about 1 mm, 900 μm, 800 μm, 750 μm, 700 μm, 650 μm, 600 μm, 550 μm, 520 μm, 510 μm, 500 μm, 480 μm, 450 μm, or 400 μm. In certain embodiments, an outer diameter of the needle is at most about 510 μm. In certain embodiments, the outer diameter of the needle is about 1 mm, 900 μm, 800 μm, 750 μm, 700 μm, 650 μm, 600 μm, 550 μm, 520 μm, 510 μm, 500 μm, 480 μm, 450 μm, or 400 μm. In certain embodiments, an outer diameter of the needle is about 510 μm. In certain embodiments, the needle is of a certain gauge, as prescribed according to ISO 7864:2016. For example, but not by way of limitation, the needle is about 19, 19.5, 20, 20.5, 21, 21.5, 22, 22.5, 23.5, 24, 24.5, 25, 25.5, 26, 26.5, or 27 gauge (ga).

In certain embodiments, the needle is at most about 19, 19.5, 20, 20.5, 21, 21.5, 22, 22.5, 23.5, 24, 24.5, 25, 25.5, 26, 26.5, or 27 ga. The needle can be at most about 25 ga. As described herein, when a comparison is made for the size of needle relative to a particular gauge size, the comparison is made between the outer diameter of the needle and the outer diameter of a standardized hypodermic needle of that particular gauge as prescribed by ISO 7864:2016. In certain other embodiments, the needle has a relatively small outer diameter and a relatively large inner diameter. In certain embodiments, the needle has a non-standard size, for instance, having a thin wall while maintaining a large inner diameter and a small outer diameter.

The total number of cells and the cell concentration inside the injector of the needle are selected based on a number of factors, for instance, the size of the cells to be injected, the type of ectopic tissue to produce, the proliferation capability of the cells, the target mass of the ectopic tissue, the size of the needle for injection, and the size of the target lymph node.

In certain embodiments, the injector as described herein receives at least about 10 million, 20 million, 30 million, 40 million, 50 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, 10 billion, 20 billion, 50 billion, or 100 billion cells for injection. In certain embodiments, the injector as described herein has about 10 million, 20 million, 30 million, 40 million, 50 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, 10 billion, 20 billion, 50 billion, or 100 billion cells for injection. In certain embodiments, the injector as described herein has at most about 10 million, 20 million, 30 million, 40 million, 50 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, 10 billion, 20 billion, 50 billion, or 100 billion cells for injection. In certain embodiments, the injector receives from about 50 million to about 200 million cells for injection.

In certain embodiments, the injector as described herein receives at least about 10 million, 20 million, 30 million, 40 million, 50 million, 60 million, 70 million, 80 million, 90 million, or 100 million hepatocytes for production of an ectopic liver. In certain embodiments, the injector as described herein has about 10 million, 20 million, 30 million, 40 million, 50 million, 60 million, 70 million, 80 million, 90 million, or 100 million hepatocytes for production of an ectopic liver. In certain embodiments, the injector as described herein has at most about 10 million, 20 million, 30 million, 40 million, 50 million, 60 million, 70 million, 80 million, 90 million, or 100 million hepatocytes for production of an ectopic liver. In certain embodiments, the injector receives from about 50 million to about 200 million cells for production of an ectopic liver.

In certain embodiments, the injector as described herein has a suspension solution of cells having at least about 30 million, 40 million, 45 million, 50 million, 55 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, or 10 billion cells per mL. In certain embodiments, the injector as described herein has a suspension solution of cells having about 30 million, 40 million, 45 million, 50 million, 55 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, or 10 billion cells per mL. In certain embodiments, the injector as described herein has a suspension solution of cells having at most about 30 million, 40 million, 45 million, 50 million, 55 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, or 10 billion cells per mL.

In certain embodiments, the injector as described herein receives a suspension solution of hepatocytes having at least about 30 million, 40 million, 45 million, 50 million, 55 million, 60 million, 70 million, 80 million, 90 million, or 100 million cells per mL for production of an ectopic liver. In certain embodiments, the injector as described herein receives a suspension solution of hepatocytes having about 30 million, 40 million, 45 million, 50 million, 55 million, 60 million, 70 million, 80 million, 90 million, or 100 million cells per mL for production of an ectopic liver. In certain embodiments, the injector as described herein receives a suspension solution of hepatocytes having at most about 30 million, 40 million, 45 million, 50 million, 55 million, 60 million, 70 million, 80 million, 90 million, or 100 million cells per mL for production of an ectopic liver.

In certain embodiments, the needle for injection of hepatocytes is selected to be at most about 25 gauge, and the needle delivers the cells including hepatocytes in a suspension solution that has at least about 50 million viable cells per mL. In certain embodiments, the population of cells inside the injector has at least about 65% viable cells.

Without wishing to be bound to a certain theory, the viability of the cells delivered into the lymph node can be important for the formation and function of the ectopic tissue. In certain embodiments, the viability percentage in the population of cells needs to be controlled. The injector, e.g., the needle, can be configured to maintain the viability of the cells during the delivery process. For instance, the needle size and the cell concentration of the suspension solution can be configured so that the viability percentage does not significantly decrease when the cells pass through the needle during cell delivery process. In certain embodiments, the cell delivery leads to less than about 20%, 15%, 10%, 9%, 8.5%, 8%, 7.5%, 7%, 6.5%, 6%, 5.5%, 5%, 4.5%, 4%, 3.5%, 3%, 2.5%, 2%, 1.5%, 1%, or 0.5% reduction in cell viability percentage in the population of cells when the cells pass through the needle. In certain embodiments, the reduction of cell viability percentage is less than about 10% when the cells pass through the needle during cell delivery (e.g., as compared to the viability of the cells prior to injection).

In certain embodiments, the methods provided herein include reducing blood supply to the liver of the subject, and delivering one or more hepatocytes into a lymph node of the subject. The reduction of blood supply to the liver of the subject can induce hepatocellular dysfunction, e.g., malfunction or death of at least some of the liver cells, and consequentially reduction or loss of function of the liver. Without wishing to be bound to a particular theory, the reduction or loss of function of liver in the subject after reduction of blood supply to the liver can have a compensatory impact on the growth of the ectopic liver in the lymph node after hepatocyte transplantation into the lymph node. In other words, the step of reducing blood supply to the liver, in certain embodiments, facilitates the formation of the ectopic liver in the lymph node, and/or, in certain embodiments, improves the functional performance of the ectopic liver in the lymph node. In certain embodiments of the methods, cell delivery is carried out by direct injection (e.g., via major surgery or percutaneous injection) of the hepatocytes or EUS-guided injection of the hepatocytes, when performed in combination with the step of reducing blood supply to the liver.

A surgical method can be used for reducing blood supply to the liver, which can involve redirecting the blood inflow from the portal vein. For instance, a transjugular intrahepatic portosystemic shunt (TIPS) procedure is performed to establish direct communication between the inflow portal vein and the outflow hepatic vein, thus the blood flow through the liver can be reduced. TIPS refers to an artificial channel within the liver that establishes communication between the portal vein and the hepatic vein. TIPS has been used as a stand-alone therapy to alleviate the detrimental splanchnic and systemic hemodynamic impact of progressive portal hypertension due to end stage liver disease. In certain embodiments, the methods disclosed herein include using TIPS in combination with hepatocyte transplant in a lymph node to produce an ectopic liver in the lymph node.

Transjugular intrahepatic portosystemic shunts can be surgically placed in the liver through a major surgery involving opening of the abdominal cavity, or a minimally invasive procedure. In certain embodiments, transjugular intrahepatic portosystemic shunts is placed under fluoroscopic guidance. Access to the liver can be obtained via the internal jugular vein in the neck. Once access to the jugular vein is confirmed, a guidewire and introducer sheath can be placed to facilitate the shunt's placement. This step can enable the access to the patient's hepatic vein by traveling from the superior vena cava into the inferior vena cava and finally the hepatic vein. Once the catheter is in the hepatic vein, a wedge pressure can be obtained to calculate the pressure gradient in the liver. Following this, carbon dioxide can be injected to locate the portal vein. Then, a special needle known as a Colapinto can be advanced through the liver parenchyma to connect the hepatic vein to the large portal vein, near the center of the liver. The channel for the shunt can be next created by inflating an angioplasty balloon within the liver along the tract created by the needle. The shunt can be completed by placing a special mesh tube known as a stent or endograft to maintain the tract between the higher-pressure portal vein and the lower-pressure hepatic vein. After the procedure, fluoroscopic images can be made to show placement.

In certain other embodiments, portacaval shunt procedure is performed to establish communication between the portal vein and the inferior vena cava, in order to reduce blood supply to the liver. Portacaval shunt can be placed by surgical methods such as, but not limited to, the procedure described in Example 2. Other surgical procedures that can be used can include end-to-side or side-to-side portocaval shunt (SSPCS), mesocaval shunts (MCS) with interposition H- or C-grafts and splenorenal shunts (SRS) (either central or distal).

In certain embodiments, hepatocytes are delivered to a lymph node after blood supply to the liver is reduced. In certain embodiments, hepatocyte transplant is performed immediately after the step of reducing blood supply to the liver. In certain embodiments, hepatocyte transplant is performed a period after the step of reducing blood supply to the liver, for instance, about 1 hour, 2 hours, 6 hours, 12 hours, 18 hours, 24 hours, 36 hours, 2 days, 3 days, 4 days, 5 days, 7 days, 10 days, 2 weeks, 3 weeks, or 4 weeks. In certain embodiments, such an interval cannot be longer than a certain amount of time, in order to avoid complete liver failure, which can be life-threatening. For example, but not by way of limitation, the interval is shorter than about 12 hours, 18 hours, 24 hours, 36 hours, 2 days, 3 days, 4 days, 5 days, 7 days, 10 days, 2 weeks, 3 weeks, or 4 weeks. Alternatively, hepatocyte transplant can also be performed shortly before the step of reducing blood supply to the liver. In certain embodiments, the interval can be shorter than about 1 hour, 2 hours, 6 hours, 12 hours, 18 hours, 24 hours, 36 hours, 2 days, 3 days, 4 days, 5 days, 7 days, 10 days, 2 weeks, or 3 weeks. The interval between the two steps can depend on the extent of the reduction in blood supply to the liver and the health condition of the subject receiving the procedures. Doctor's medical assessment on a case-by-case basis can be involved in determining the interval between the two steps as described herein.

Transplant rejection can be a problem associated with any transplantation procedure involving implant of non-autologous organs or cells. Immunosuppression can be applied to prevent or ameliorate the transplant rejection induced by procedures according the methods of the present disclosure. For example, immunosuppressant drugs can be administered to the subject shortly before or immediately after cell transplantation is completed, or at about 1 hour, 2 hours, 6 hours, 12 hours, 18 hours, 24 hours, 36 hours, 2 days, 3 days, 4 days, 5 days, 7 days, 10 days, 2 weeks, 4 weeks, 6 weeks, 2 months, 3 months, 4 months, 5 months, 6 months, 9 months, 12 months, 18 months, 2 years, 3 years, 4 years, or even longer after the procedure.

Different approaches of immunosuppression can be applied herein. For example, but not by way of limitation, the subject is administered an immunosuppressant for induction immunosuppression, which can include all medications given immediately after transplantation in intensified doses for the purpose of preventing acute rejection. Non-limiting examples of associated medications can include Methyl-prednisolone, Atgam, Thymoglobulin, OKT3, Basiliximab, Solumedrol, and Daclizumab. The subject can also be administered an immunosuppressant for maintenance immunosuppression, which can include all immunosuppressive medications given before, during or after transplant with the intention to maintain them long-term. For example, but not by way of limitation, Prednisone, Cyclosporine, Tacrolimus, Mycophenolate Mofetil, Azathioprine, Prograf, or Rapamycin can be used for maintenance immunosuppression as described herein. In certain embodiments, the subject can also be administered an immunosuppressant for anti-rejection immunosuppression, which can include all immunosuppressive medications given for the purpose of treating an acute rejection episode during the initial post-transplant period or during a specific follow-up period, e.g., up to 30 days after the diagnosis of acute rejection. Non-limiting examples of associated medications can include Methyl-prednisolone, Atgam, OKT3, Thymoglobulin, Basiliximab, or Daclizumab. Other examples of immunosuppressant that can be used in the subject methods can also include other steroids (such as corticosteroids, dexamethasone, and prednisone), Cox-1 and Cox-2 inhibitors, macrolide antibiotics (such as rapamycin and tacrolimus), and other substances that limit, reduce, or suppress B-cell, T-cell, and/or other innate immune activity.

4. Production of Ectopic Tissue from Transplanted Cells

The methods and systems provided herein can be applied to transplant various types of cells, including, but not limited to, hepatocytes, kidney cells or kidney tissue fragments, pancreatic cells or islets, thymic cells or thymus fragments, or lung cells or lung tissue fragments. The cells transplanted into the lymph node can engraft and form ectopic tissue that can supplement or augment one or more functions of a normal organ of a subject.

The cells to be transplanted into a lymph node can be either a homogenous cell population or a heterogeneous cell population, depending on the purpose of the cell transplant. For example, in certain embodiments, a population of homogeneous hepatocytes is delivered into a lymph node to produce an ectopic liver. In certain embodiments, when growing an ectopic liver, a heterogeneous population of cells, e.g., hepatocytes with additional other liver parenchymal cells, is delivered into a lymph node. In certain embodiments, a population of heterogeneous kidney cells or kidney fragments is delivered into a lymph node for the purpose of generating an ectopic kidney in the lymph node. In certain embodiments, an embryonic kidney from a donor subject or a kidney organoid that are generated by in vitro differentiation methods (such as those described in International Patent Publication Nos. WO2014182885A2, WO2019006127A1, and WO2018227101A1, each of which is incorporated herein by reference) is obtained, and is processed (e.g., minced or grinded) into small fragments and resuspended in a liquid to form a solution to be delivered into a lymph node. The solution includes different types of cells that constituting the embryonic kidney or the kidney organoid. In certain embodiments, a population of heterogeneous pancreatic cells is delivered into the lymph node for generating an ectopic pancreas.

The methods and systems provided herein can involve delivering a therapeutically-effective amount of cells into the lymph node of a subject. The term "therapeutically-effective amount" as used herein when referring to a population of cells to be transplanted or delivered can mean the amount of relevant cells in the population of cells, e.g., the cells to be transplanted, or composition including the cells to be transplanted, that is effective for producing a desired therapeutic effect in the subject receiving the cell transplant in the lymph node at a reasonable benefit/risk ratio applicable to any medical treatment. For example, but not by way of limitation, the amount of a population of cells transplanted into a subject is sufficient to produce a statistically significant, measurable change in one or more symptoms of the disease or condition the transplantation is intended to treat, e.g., end-stage liver disease or renal disease. Determination of a therapeutically effective amount is dependent on the intended medical purpose of applying the subject methods or systems. A therapeutically effective amount can vary with the subject's history, age, condition, sex, as well as the severity and type of the medical condition in the subject, and administration of other pharmaceutically active agents.

Depending on the intended purpose of applying the methods and systems provided herein, different amounts of cells can be delivered into a lymph node for growing an ectopic tissue. There can be at least about 1 million, 2 million, 3 million, 4 million, 5 million, 7 million, 9 million, 10 million, 15 million, 20 million, 30 million, 40 million, 45 million, 50 million, 55 million, 60 million, 70 million, 80 million, 90 million, 100 million, 150 million, 200 million, 300 million, 500 million, 750 million, 800 million, 900 million, 1 billion, 5 billion, 10 billion, 20 billion, 30 billion, 50 billion, or even more cells delivered per lymph node. In certain embodiments, about 10 million, 15 million, 20 million, 30 million, 40 million, 45 million, 50 million, 55 million, 60 million, 70 million, 80 million, 90 million, or 100 million cells can be delivered into a single lymph node. In certain embodiments, about 50 million to about 200 million of cells can be delivered in a single lymph node.

The population of cells to be delivered can have at least about 40%, 45%, 50%, 55%, 60%, 65%, 66%, 67%, 68%, 69%, 70%, 71%, 72%, 73%, 74%, 75%, 80%, 85%, 90%, 95%, or about 100% viable cells. Measures available to promote cell viability can be applied in order to maintain the cell viability level in the population of cells to be delivered. In certain embodiments, prior to cell delivery, the viability status of the population of cells (e.g., viability percentage or other cell viability parameters) can be measured in order to ensure viable cell population to be delivered and consequently functional ectopic tissue can be produced in the lymph node.

In non-limiting embodiments, the ectopic tissue can be formed at least about 5 days, 10 days, 15 days, 20 days, 25 days, 30 days, 35 days, 40 days, 45 days, 50 days, 55 days, 60 days, 65 days, 70 days, 75 days, 80 days, 85 days, 90 days, 95 days, 100 days, 110 days, 120 days, 130 days, 140 days, 150 days, 160 days, 170 days, 180 days, 190 days, or about 200 days after transplantation of the disclosed various types of cells into a lymph node. For example, but not by way of limitation, hepatocytes can be delivered into lymph nodes via EUS, and the engrafted hepatocytes can form a liver tissue about 60, about 90, or about 150 days after the transplantation of the hepatocytes. In non-limiting embodiments, the ectopic tissue can be formed within about 5 days, 10 days, 15 days, 20 days, 25 days, 30 days, 35 days, 40 days, 45 days, 50 days, 55 days, 60 days, 65 days, 70 days, 75 days, 80 days, 85 days, 90 days, 95 days, 100 days, 110 days, 120 days, 130 days, 140 days, 150 days, 160 days, 170 days, 180 days, 190 days, or about 200 days after transplantation of the disclosed various types of cells into a lymph node. For example, but not by way of limitation, hepatocytes can be delivered into lymph nodes via EUS, and the engrafted hepatocytes can start forming a liver tissue within about 60, about 90, or about 150 days after the transplantation of the hepatocytes.

The cells to be delivered can be obtained from different sources and via a number of different methods. The cells can be allogeneic, xenogeneic, or autologous to the subject. The cells can be obtained directly from a live donor tissue. For example, hepatocytes are isolated and prepared for transplant according to the methods described in U.S. Pat. Nos. 9,125,891B2 and 6,610,288B1, U.S. Patent Publication No. 20120045764A1 and 20040110289A1, each of which is incorporated herein by reference. In certain embodiments, the cells to be delivered are obtained from in vitro sources. Stem cells, such as embryonic stem cells, induced pluripotent stem cells, trophoblast stem cells, or any other type of pluripotent or multipotent stem cells, can be cultured in vitro and differentiated into certain types of cells or cell populations that are suitable for the purposes of applying the methods and systems provided herein. For example, as described above, kidney organoids or pancreatic islets are obtained using in vitro differentiation methods and they are prepared for transplantation procedures described herein. The cells to be delivered can also be stored, e.g., cryopreserved, prior to transplantation. Standard cryopreservation and recovery protocols can be used so along as the cell viability level cis suitable for the subsequent cell delivery and ectopic tissue formation in the lymph node. In certain embodiments, the cells to be delivered are genetically modified so that one or more genes of the cells are modified, or the cells are modified to express one or more exogenous genes. Any available gene editing methods, such as homologous recombination, transposase/transposon, Zinc Finger nuclease, TALEN, and CRIPSR, e.g., CRISPR-Cas9, technologies, can be applied for gene modification of the cells to be delivered.

The cells can be prepared and suspended in solutions for transplant. In certain embodiments, the suspension solution containing the cell population can further include pharmaceutically acceptable excipients, diluents, or carriers. As used herein, the term "pharmaceutically acceptable" can refer to those compounds, materials, compositions, and/or dosage forms which are, within the scope of sound medical judgment, suitable for use in contact with the tissues of the subject (e.g., human subject or nonhuman animals) without excessive toxicity, irritation, allergic response, or other problem or complication, commensurate with a reasonable benefit/risk ratio.

As used herein, the term "solution" can include a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid to the extent that easy syringability exists. The solution can be stable under the conditions of manufacture and storage and preserved against the contaminating action of microorganisms such as bacteria and fungi through the use of, for example, parabens, chlorobutanol, phenol, ascorbic acid, thimerosal, and the like. Solutions of the present disclosure can be prepared by incorporating viable, functional cells as described herein in a pharmaceutically acceptable carrier or diluent and, as required, other ingredients enumerated above, followed by filtered sterilization.

Non-limiting examples of substances or materials that can serve as pharmaceutically-acceptable excipients for the purpose of the present disclosure can include: sugars, such as lactose, glucose and sucrose; starches, such as corn starch and potato starch; cellulose, and its derivatives, such as sodium carboxymethyl cellulose, methylcellulose, ethyl cellulose, microcrystalline cellulose and cellulose acetate; powdered tragacanth; malt; gelatin; lubricating agents, such as magnesium stearate, sodium lauryl sulfate and talc; cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol (PEG); esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; bulking agents, such as polypeptides and amino acids; serum component, such as serum albumin, HDL and LDL; C2-C12 alcohols, such as ethanol; and other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. As used herein, the term "pharmaceutically-acceptable excipient" can refer to a pharmaceutically-acceptable material, composition or vehicle, such as a liquid or solid filler, diluent, carrier, manufacturing aid (e.g., lubricant, talc magnesium, calcium or zinc stearate, or stearic acid), or solvent encapsulating material, involved in carrying or transporting the subject compound, materials, or cells, to an organ or portion of the body. Each excipient must be "acceptable" in the sense of being compatible with the other ingredients of the formulation, e.g., the cells to be transplanted, and not injurious to the subject.

After being delivered into the lymph node, the cells of the present disclosure can engraft, proliferate, and produce an ectopic tissue in the lymph node. As used herein, the term "engraft" or grammatically equivalents thereof can refer to the process that the one or more cells are implanted in a target lymph node and survive and becomes biologically active (e.g., performing cellular function) within the lymph node. As used herein, the term "proliferate" or grammatically equivalents thereof can refer to the process that a cell experiences one or more series of mitosis and generate a number of offspring cells, the proliferation process can result in exponential increase in cell count. In certain embodiments, the cells proliferate at a high level, such that the mass of the ectopic tissue eventually produced is significantly higher than the original mass of the cells delivered to the lymph node. In certain embodiments, the cell proliferation is at a moderate level. In certain embodiments, the mass increase is at least about 1.2 times, 1.5 times, 2 times, 2.5 times, 3 times, 3.5 times, 4 times, 4.5 times, 5 times, 6 times, 7 times, 7.5 times, 8 times, 9 times, 10 times, 12 times, 15 times, 17.5 times, 20 times, 30 times, 40 times, 50 times, 60 times, 70 times, 80 times, 90 times, 100 times, 120 times, 150 times, 200 times, 300 times, 400 times, 500 times, or 1000 times, e.g., compared to the mass of the cells as originally transplanted. In certain embodiments, the number of cells increases by at least about 1.2 times, 1.5 times, 2 times, 2.5 times, 3 times, 3.5 times, 4 times, 4.5 times, 5 times, 6 times, 7 times, 7.5 times, 8 times, 9 times, 10 times, 12 times, 15 times, 17.5 times, 20 times, 30 times, 40 times, 50 times, 60 times, 70 times, 80 times, 90 times, 100 times, 120 times, 150 times, 200 times, 300 times, 400 times, 500 times, or 1000 times, e.g., compared to the number of the cells as originally transplanted.

In certain embodiments, vascularization can take place in the lymph node receiving the cell transplant, e.g., there can be blood vessels infiltrating and forming vasculature network within the lymph node, in certain embodiments, within the ectopic tissue. In certain embodiments, the infiltrating vasculature network can form the basis of blood supply to the ectopic tissue. In certain embodiments, the infiltrating vasculature network can help transport metabolic products or materials to and/or from the ectopic tissue. For example, but not by way of limitation, an ectopic liver can produce glycogen, glucose, and/or bile, which can be transported into the main blood stream by the vasculature network formed inside the transplantation site (the lymph node). In certain embodiments, an ectopic pancreas can produce and secrete insulin, glucagon, and/or somatostatin, which can also be introduced into the main blood stream of the subject's body via the vasculature network formed inside the lymph node. In certain embodiments, the lymphatic circulation system also serves as a transportation channel for the substances produced by the ectopic tissue. The lymphatic system, in certain embodiments, can thus supply provide such substances to the blood circulation system via their crosstalk in other parts of the body.

5. Diseases and Conditions

The methods and systems can be applied to treat a disease or condition in a subject. In certain embodiments, the methods and systems find use in growing one or more ectopic tissues in lymph nodes, which supplement or augment function of an organ to the subject and, as a result, can ameliorate one or more symptoms of or cure the disease or condition the subject is suffering from.

A. Liver Diseases and Conditions

In certain embodiments, the methods and systems can be used to deliver hepatocytes into a lymph node of the subject, allowing the hepatocytes to engraft and produce an ectopic liver in the lymph node. The ectopic liver can have one or more functions that a normal healthy liver organ can perform, such as, but not limited to, production of bile, which can help clear waste and break down fats in the small intestine during digestion; production of plasma proteins, e.g., albumin; production of cholesterol, phospholipids, and lipoproteins to help carry fats through the body; regulation of blood glucose by conversion of excess glucose into glycogen for storage (glycogenesis) and depolymerization of glycogen (glyconolysis) when glucose is needed; conversion of excess carbohydrates and proteins into fatty acids and triglyceride; deamination and transamination of amino acids; conversion of the non-nitrogenous part of amino acids to glucose or lipids; oxidization of triglycerides to produce energy; processing of hemoglobin for use of its iron content (the liver stores iron); conversion of poisonous ammonia to urea; blood dialysis to clear certain drugs and other poisonous substances; synthesis of clotting factors necessary for blood coagulation; resisting infection by producing immune factors and removing bacteria from the bloodstream; clearance of bilirubin from red blood cells.

In certain embodiments, the methods and systems can be used for treating a number of different liver diseases or conditions. Such liver diseases or conditions can involve liver failure or reduction in one or more of liver functions. Non-limiting examples of liver diseases and/or disorders that can be treated by the methods of the present disclosure include acute liver failure, cirrhosis, liver cancer, hepatitis, fatty liver disease and non-alcoholic fatty liver disease. The liver condition can be associated with metabolic disorders (e.g., pediatric metabolic disorders), including, but not limited to, tyrosinemia, maple syrup urine disease, phenylketonuria, Crigler-Najjar syndrome, oxalosis, hyperoxaluria, hemochromatosis, Alpha-1 antitrypsin deficiency, Wilson disease, familial intrahepatic cholestasis syndromes, and familial amyloid polyneuropathy. The present methods and systems can find particular use in treating end stage liver disease and/or liver fibrosis, for instance, those caused by Hepatitis B infection, Hepatitis C infection, alcohol consumption, cirrhosis, nonalcoholic steatohepatitis, or hemochromatosis.

In certain embodiments, the methods and systems provided herein when applied to a subject in need thereof ameliorate one or more symptoms associated with the liver disease or condition, e.g., recovery of one or more liver functions, and/or in certain embodiments, prolong the survival of the subject experience life-threatening liver disease or condition before the cell transplant. For example, the subjects receiving the hepatocyte transplant according to the present disclosure can find improvement in the results of their liver function tests, such as alanine transaminase (ALT) test, aspartate aminotransferase (AST) test, alkaline phosphatase (ALP) test, albumin test, bilirubin test. Such improvement can be at least about 10%, 20%, 30%, 40%, 50%, 60%, 70%, 80%, 90%, or about 100% recovery as compared to other healthy subject or as compared to the test results of the same subject before having the liver disease or condition. In certain embodiments, the lifespan of the subject receiving the hepatocyte transplantation is prolonged for at least about 6 months, 9 months, 1 year, 2 years, 3 years, 4 years, 5 years, 6 years, 7 years, 8 years, 9 years, 10 years, 12 years, 15 years, 18 years, 20 years, 25 years, 30 years, 40 years, 50 years, 60 years, or even longer.

B. Kidney Diseases and Conditions

In certain embodiments, the methods and systems can be used to deliver kidney cells or kidney tissue fragments into a lymph node of the subject, allowing the kidney cells to engraft and produce an ectopic kidney in the lymph node. The ectopic kidney can have one or more functions that a normal healthy kidney organ can perform. For instance, the ectopic kidney can perform, to some extent or to the full extent, the main function of a kidney: production of urine, which can involve filtration of substances of small molecular weights (e.g., metabolic waste) from blood to produce an ultrafiltrate that eventually becomes urine while retaining cells and large proteins in blood; and reabsorption of certain substances (e.g., ions, glucose) from the ultrafiltrate into the peritubular capillary. In certain embodiments, the ectopic kidney can also participate in the maintenance of whole-body homeostasis as a normal kidney can do, such as, but not limited to, acid-base balance, electrolyte concentrations, extracellular fluid volume, and blood pressure.

In certain embodiments, the methods and systems find use in treating a number of different renal diseases or conditions. Such renal diseases or conditions can involve renal failure or reduction in one or more of renal functions. Non-limiting examples of renal diseases and/or disorders that can be treated by the methods of the present disclosure include acute kidney failure, chronic kidney disease, glomerulonephritis, Lupus, polycystic kidney disease, nephropathy, nephrosis, kidney malformations and kidney cancer. The present methods and systems can find particular use in treating end stage renal disease (kidney failure), for instance, those caused by diabetes, autoimmune diseases (e.g., lupus and IgA nephropathy), genetic diseases (e.g., polycystic kidney disease), nephrotic syndrome, and urinary tract problems.

In certain embodiments, the methods and systems provided herein when applied to a subject in need thereof ameliorate one or more symptoms associated with the kidney disease or condition, e.g., recovery of one or more kidney functions, and/or in certain embodiments, prolong the survival of the subject experience life-threatening kidney disease or condition before the cell transplant. For example, but not by way of limitation, the subjects receiving the transplant of kidney cell or fragments according to the present disclosure find improvement in the results of their kidney function tests, such as blood tests for serum creatinine, glomerular filtration rate (GFR), blood urea nitrogen (BUN). Such improvement can be at least about 10%, 20%, 30%, 40%, 50%, 60%, 70%, 80%, 90%, or about 100% recovery as compared to other healthy subject or as compared to the test results of the same subject before having the renal disease or condition. In certain embodiments, the lifespan of the subject receiving the transplant of kidney cells or fragments can be prolonged for at least about 6 months, 9 months, 1 year, 2 years, 3 years, 4 years, 5 years, 6 years, 7 years, 8 years, 9 years, 10 years, 12 years, 15 years, 18 years, 20 years, 25 years, 30 years, 40 years, 50 years, 60 years, or even longer.

C. Pancreatic Diseases and Conditions

In certain embodiments, the methods and systems are used to deliver pancreatic cells (e.g., pancreatic $\beta$, $\alpha$, $\delta$, $\zeta$, or $\gamma$ cells) or islets into a lymph node of the subject, allowing the pancreatic cells or islets to engraft and produce an ectopic pancreas in the lymph node. The ectopic pancreas can have one or more functions that a normal healthy pancreas organ can perform. For example, but not by way of limitation, the ectopic pancreas secretes one or more of insulin, glucagon, somatostatin or pancreatic polypeptide. In certain embodiments, the ectopic pancreas secretes the one or more endocrine hormones properly in response to physiological stimuli. In certain embodiments, the ectopic pancreas secretes insulin in response to increase in blood glucose concentration and/or secrete glucagon in response to decrease in blood glucose concentration, which can help maintain the homeostasis of blood glucose level. Such secretion response can be proportional to the change in physiological stimuli. For example, the more the increase is in blood glucose, the more insulin secreted by the ectopic pancreas, the ratio of which can be, at least partially equivalent to or similar to a normal healthy pancreas in other healthy subject or the pancreas of the same subject before suffering the pancreatic disease.

In certain embodiments, the methods and systems find use in treating a number of different pancreatic diseases or conditions. Such pancreatic diseases or conditions can involve pancreatic failure or reduction in one or more of pancreatic functions. The pancreatic diseases or conditions treated by the methods and systems provided herein can be endocrine pancreatic diseases or conditions. Non-limiting examples of pancreatic diseases and/or disorders that can be treated by the methods of the present disclosure include acute pancreatitis, chronic pancreatitis, hereditary pancreatitis, and pancreatic cancer. The present methods and systems can find particular use in treating pancreas failure or other situations where pancreas transplant is needed.

In certain embodiments, the methods and systems provided herein when applied to a subject in need thereof ameliorate one or more symptoms associated with the pancreatic disease or condition, e.g., recovery of one or more pancreatic functions, and/or in certain embodiments, prolong the survival of the subject experience life-threatening pancreatic disease or condition before the cell transplant. For example, but not by way of limitation, the subjects receiving the transplant of pancreatic cells or islets according to the present disclosure can find improvement in blood glucose control. Such improvement can be at least about 10%, 20%, 30%, 40%, 50%, 60%, 70%, 80%, 90%, or about 100% recovery as compared to other healthy subject or as compared to the test results of the same subject before having the pancreatic disease or condition. In certain embodiments, the lifespan of the subject receiving the transplant of pancreatic cells or islets can be prolonged for at least about 6 months, 9 months, 1 year, 2 years, 3 years, 4 years, 5 years, 6 years, 7 years, 8 years, 9 years, 10 years, 12 years, 15 years, 18 years, 20 years, 25 years, 30 years, 40 years, 50 years, 60 years, or even longer.

D. Immune System Dysfunction/Immunodeficiency Disorders and Conditions

In certain embodiments, the methods and systems are used to deliver thymic cells or thymus fragments into a lymph node of the subject, allowing the thymic cells or fragments to engraft and produce an ectopic thymus in the lymph node. In certain embodiments, the ectopic thymus supplements or augments one or more functions that a normal healthy thymus organ can perform. For example, but not by way of limitation, the ectopic thymus can participate in immunomodulation of the body for its participation of T cell growth, development, maturation, and selection. Production of ectopic thymus according to the present disclosure can find use in augmenting or modulating immune system function in subjects having immune system dysfunction, for instance, in aged or elderly subject (e.g., older than 50, 55, 60, 65, 70, 75, 80, or 85 years old), or in subjects having immunodeficiency disorders or conditions, such as X-linked agammaglobulinemia (XLA), common variable immunodeficiency (CVID), severe combined immunodeficiency (SCID), severe burns, chemotherapy, radiation, diabetes, malnutrition, adaptive immunodeficiency syndrome (AIDS), leukemia, severe viral infections, and multiple myeloma.

In certain embodiments, thymic cells or fragments from a donor subject are introduced into a lymph node of the recipient subject prior to organ or other cell transplant from the same donor subject. The production of the ectopic thymus in the lymph node can induce tolerance n the recipient subject to the donor subject, which can be beneficial for the subsequent organ or cell transplant. The thymic cell transplant, in these embodiments, can be performed at least about 5 days, 1 week, 2 weeks, 3 weeks, 4 weeks, 1 month, 2 months, 3 months, 4 months, 6 months, 9 months, or 1 year before the organ or other cell transplant, so that the proper immune tolerance to the donor subject can be established in the recipient. The thymic cell transplant can be described herein can be applied in conjunction with any type of organ transplant or transplant of any other cell types, and can reduce the transplant rejection response seen in a recipient receiving otherwise the same organ or cell transplant but without the thymic cell transplant according to the present disclosure.

The lifespan of the subject receiving the transplant of cells according to the present disclosure can be prolonged for at least about 6 months, 9 months, 1 year, 2 years, 3 years, 4 years, 5 years, 6 years, 7 years, 8 years, 9 years, 10 years, 12 years, 15 years, 18 years, 20 years, 25 years, 30 years, 40 years, 50 years, 60 years, or even longer.

E. Lung Diseases and Conditions

In certain embodiments, the methods and systems are used to deliver lung cells or lung tissue fragments into a lymph node of the subject, allowing the lung cells or fragments to engraft and produce an ectopic lung in the lymph node. The ectopic lung can have one or more functions that a normal healthy pancreas lung can perform. For instance, the ectopic lung can patients with chronic obstructive pulmonary disease (COPD). The ectopic lung can increase the pulmonary functional mass, which can be severely decreased by the progressive fibrosis in patients with COPD. In certain embodiments, patients experiencing lung reduction procedures that wouldn't be candidates for standard lung transplantation can be suitable for the transplantation of lung cells within the peribronchial lymph nodes.

In certain embodiments, the methods and systems find use in treating a number of different lung diseases or conditions. Such lung diseases or conditions can involve lung failure or reduction in one or more of lung functions. Non-limiting examples of lung diseases and/or disorders that can be treated by the methods of the present disclosure include chronic obstructive pulmonary disease (COPD). COPD can be caused by: cigarette smoke and further tobacco use, pollutions (chemical, dust or toxic substances) and fumes, genetic disorders (e.g., alpha-l-antiytrypsin, cystic fibrosis), chronic asthma, emphysema, chronic bronchitis, or idiopathic pulmonary fibrosis.

In certain embodiments, the methods and systems provided herein can ameliorate one or more symptoms associated with the lung disease or condition, e.g., recovery of one or more lung functions, and/or in certain embodiments, prolong the survival of the subject experience life-threatening lung disease or condition before the cell transplant.

6. Subjects

Subject that can receive cell transplant according to the present disclosure can be any human patient, such as an ESLD patient, a patient with kidney failure, a patient with type I diabetes, or a patient awaiting organ transplant. In certain embodiments, the subject is in a particular stage of medical treatment.

A subject receiving a cell transplant according to the present disclosure can be of any age and can be an adult, newborn, infant or child. In certain embodiments, the subject is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). Furthermore, a subject can be male or female.

The suitability of a subject to receive a cell transplant according to the present disclosure can be determined by a certified doctor. In certain embodiments, comprehensive assessment of the subject's health condition can be required prior to performing the cell transplantation. In certain embodiments, the requirement for the subject's health condition can be significantly lower than other organ or cell transplant procedure. Without wishing to be bound to a particular theory, the minimally invasive procedure according to the present disclosure can significantly reduce the risk of the surgical procedure as compared to major surgeries that are typically conducted for organ transplant. In addition, given that the cells are to be transplanted into one or more lymph nodes, rather than the diseased organ, the requirement can be further significantly lower as there can be no prerequisite conditions for the diseased organ.

Any of the methods and systems disclosed herein can also be used on a non-human subject, such as a laboratory or farm animal for research purpose or veterinary medicine purpose. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, or a cow.

7. Systems

The present disclosure further provides systems for transplanting cells and growing a functional ectopic tissue in lymph node. The system can include an endoscope and an injector having a needle and one or more cells in a suspension solution contained therein. The endoscope and the needle can be configured to advance together along a body lumen (e.g., GI tract, respiratory tract, or urinary tract) or a closed body cavity (e.g., abdominal cavity, pelvis cavity, or thoracic cavity) of the subject, and the injector can be configured to deliver the one or more cells via the needle.

As discussed above, in certain embodiments, the suspension solution can have at least about 30 million, 40 million, 45 million, 50 million, 55 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, or 10 billion cells per mL. In certain embodiments, the injector as described herein has a suspension solution of cells having about 30 million, 40 million, 45 million, 50 million, 55 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, or 10 billion cells per mL. In certain embodiments, the injector as described herein has a suspension solution of cells having at most about 30 million, 40 million, 45 million, 50 million, 55 million, 60 million, 70 million, 80 million, 90 million, 100 million, 200 million, 300 million, 400 million, 500 million, 600 million, 700 million, 800 million, 900 million, 1 billion, 3 billion, 5 billion, 8 billion, or 10 billion cells per mL.

In certain embodiments, the injector as described herein has a suspension solution of hepatocytes having at least about 30 million, 40 million, 45 million, 50 million, 55 million, 60 million, 70 million, 80 million, 90 million, or 100 million cells per mL for production of an ectopic liver. In certain embodiments, the injector as described herein has a suspension solution of hepatocytes having about 30 million, 40 million, 45 million, 50 million, 55 million, 60 million, 70 million, 80 million, 90 million, or 100 million cells per mL for production of an ectopic liver. In certain embodiments, the injector as described herein has a suspension solution of hepatocytes having at most about 30 million, 40 million, 45 million, 50 million, 55 million, 60 million, 70 million, 80 million, 90 million, or 100 million cells per mL for production of an ectopic liver.

As discussed above, in certain embodiments, the needle can have an inner diameter of at most about 700 μm, 600 μm, 500 μm, 450 μm, 400 μm, 300 μm, 260 μm, 250 μm, or 200 μm. In certain embodiments, the needle has an inner diameter of at most about 260 μm. In certain embodiments, the inner diameter of the needle is about 700 μm, 600 μm, 500 μm, 450 μm, 400 μm, 300 μm, 260 μm, 250 μm, or 200 μm. In certain embodiments, the inner diameter of the needle is about 260 μm. The needle can have an outer diameter of at most about 1 mm, 900 μm, 800 μm, 750 μm, 700 μm, 650 μm, 600 μm, 550 μm, 520 μm, 510 μm, 500 μm, 480 μm, 450 μm, or 400 μm. In certain embodiments, an outer diameter of the needle is at most about 510 μm. In certain embodiments, the outer diameter of the needle is about 1 mm, 900 μm, 800 μm, 750 μm, 700 μm, 650 μm, 600 μm, 550 μm, 520 μm, 510 μm, 500 μm, 480 μm, 450 μm, or 400 μm. In certain embodiments, an outer diameter of the needle is about 510 μm. In certain embodiments, the needle is of a certain gauge, as prescribed according to ISO 7864:2016. For example, but not by way of limitation, the needle is about 19, 19.5, 20, 20.5, 21, 21.5, 22, 22.5, 23.5, 24, 24.5, 25, 25.5, 26, 26.5, or 27 gauge (ga). In certain embodiments, the needle is at most about 19, 19.5, 20, 20.5, 21, 21.5, 22, 22.5, 23.5, 24, 24.5, 25, 25.5, 26, 26.5, or 27 ga. For example, but not by way of limitation, the needle of the system can be at most about 25 ga. In certain, embodiments, the needle has a non-standardized size, for instance, having a thin wall while maintaining a large inner diameter and a small outer diameter.

The systems and methods provided herein can be particular useful for cells of an average diameter of about 20 μm, for instance, hepatocytes. Without wishing to be bound by a certain theory, the size of the cells to be delivered can a contributing factor for determining the working cell concentration in the suspension solution, the inner diameter of the needle used for cell delivery, and cell viability level in the injector before cell delivery and post cell delivery. For cells of an average diameter of less than 20 μm, the needle size can be smaller than 25 ga, while the cell concentration and total cell number in the suspension solution can be higher as compared to cells of average diameter of about 20 μm, for instance, the parameters as discussed above. On the other hand, for cells of an average diameter of more than 20 μm, the needle size can be, for example, bigger than 25 ga, while the cell concentration and total cell number in the suspension can be lower as compared to cells of average diameter of about 20 μm, for instance, the parameters as discussed above.

8. Kits

The present disclosure further provides kits containing materials useful for performing any of the methods disclosed herein. In certain embodiments, the kit includes a container containing one or more cells disclosed herein. In certain embodiments, the cells can be provided in the container frozen. In certain embodiments, the cells can be provided in a solution, e.g., a media. In certain embodiments, the container can include from about 10 million to about 500 million cells. In certain embodiments, the container can comprise a homogenous cell population. Alternatively, the container can contain a heterogenous cell population. Non-limiting examples of cells that can be provided in the container include hepatocytes, kidney cells or kidney tissue fragments, pancreatic cells or islets, thymic cells or thymus tissue fragments, or lung cells or lung tissue fragments.

In certain embodiments, the kit can further include a second container that comprises a solution for introducing the cells into a lymph node, as disclosed herein.

In certain embodiments, the kit can further include a device (or system) for delivering the cells to a lymph node as disclosed herein. In certain embodiments, the kit can further include an endoscope as disclosed herein. In certain embodiments, the endoscope is coupled to the needle. For example, but not by way of limitation, the kit can include a needle and/or endoscope for delivering the cells to a lymph node as disclosed herein. Non-limiting examples of such delivery devices are disclosed in the Systems section above.

EXAMPLES

The following examples are provided to further illustrate some embodiments of the present invention, but are not intended to limit the scope of the invention; it will be understood by their exemplary nature that other procedures, methodologies, or techniques known to those skilled in the art can alternatively be used.

Example 1. Hepatocyte Isolation for
Transplantation and Viability Test

This example demonstrates that the viability of the isolated hepatocytes is not significantly affected when the cell suspension is delivered through needles of certain sizes according to the present disclosure. This example demonstrates that hepatocytes isolated and delivered according to one exemplary method of the present disclosure can have viability suitable for transplantation.

Liver cells were isolated according to the following protocol. First, the left hepatic lobe was obtained surgically from a donor dog and transported under cold storage technique (static preservation with Belzer solution at 4° C.) in a double bag container with ice for further processing. Liver cells were isolated using the two-step collagenase perfusion method described by Seglen (Seglen P O, Preparation of isolated rat liver cells. Methods Cell Biol, 1976; 13:29-63). Briefly, a portal cannula or cannula in any large vessel was placed. The liver was perfused with EDTA solution (0.02%) at 37° C., at a flow rate of 50 ml per minute for 10 minutes in a culture dish. Subsequently, the collagenase solution (37° C.) was recirculated through the liver sample at the same flow rate. Ten minutes later, the liver capsule was disrupted, and the digested liver parenchyma was suspended in the ice-cold Hanks' solution or Plasma-Lyte A solution containing calcium gluconate and human serum albumin. The resulting liver cell suspension was filtered and washed for three times.

Figure 3:
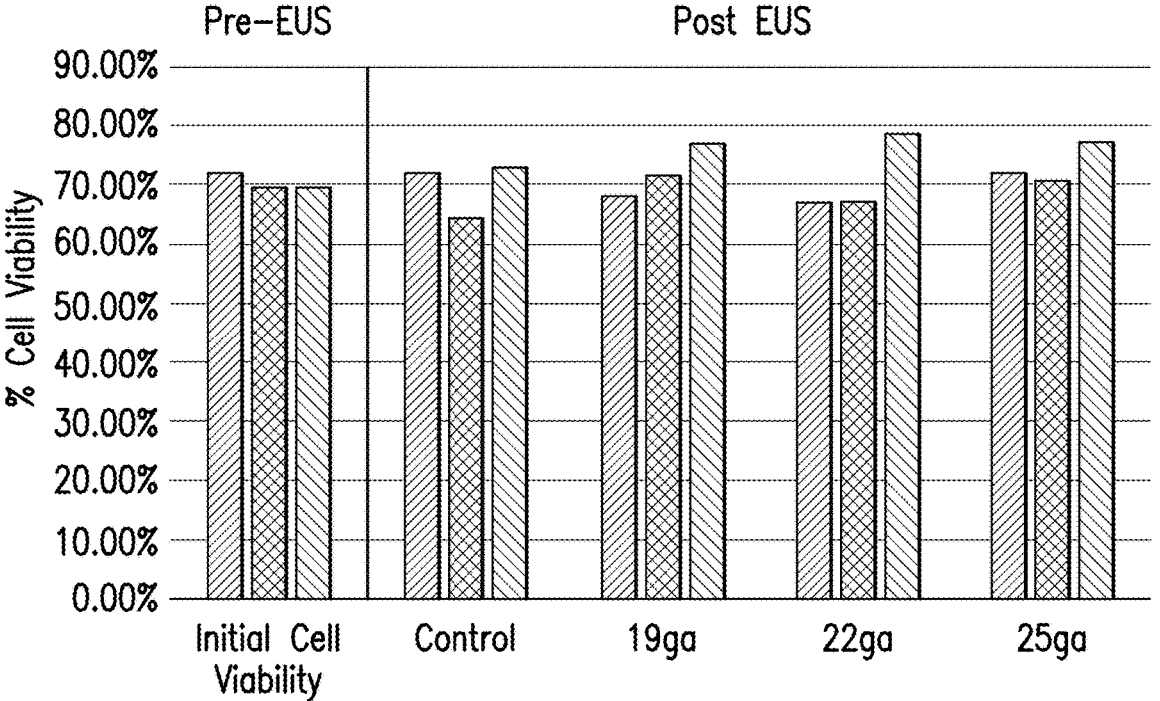
FIG. 3 is a bar graph summarizing cell viability percentage of different batches of hepatocytes that were isolated from donor animals and passed through needles of different gauges.

Trypan blue exclusion test was used to ascertain the viability of isolated hepatocytes in the suspension solutions at different steps throughout the experiments described below. In these experiments, different batches of suspension solutions that have different cell concentrations were tested for the cell viability before and after passing through the EUS FNA needles of different gauges. FIG. 3 is a plot summarizing the cell viability results obtained from the experiments of the two batches of cells. As shown in the figure, most, if not all tested solutions, before and after passing through any tested EUS needle, had similar cell viability levels.

Needles Used in the Experiments:

19 gauge (19 ga) needle (Covidien: Ref #DSN-19-01): approximate dead volume is 1.2 mL.

22 gauge (22 ga) needle (Covidien: Ref #N22-05): approximate dead volume is 0.5 mL.

25 gauge (25 ga) needle (Covidien: Ref #DSN-25-01): approximate dead volume is 1.1 mL.

Batch #1:

Donor ID #: 6303.

Initial viability after liver digestion and single cell hepatocyte isolation: 59.5%. For a total of 4.24 billion live hepatocytes (5.3 M/mL with a total of 800 mL solution).

Cell viability post 3-wash cycle and ready for transplantation: 72.04%. For a total of 429 million live hepatocytes (2.86 M/mL with a total of 150 mL solution used out of 800 mL).

The 429 million live hepatocytes were resuspended in around 20 ml and tested for viability using 19, 22 and 25 ga EUS needles. Table 1 summarizes the viability scores obtained in different groups tested in this experiment. Control represents the solution that was not pushed through any EUS needle but was handled otherwise the same before the post-test viability assessment.

TABLE 1

| | Viability Results of Batch #1 | | |
| --- | --- | --- | --- |
| EUS Needle | Cell Viability | | Concentration of |
| Gauge | Pre-Test | Post-Test | cells out of needle |
| Control | 72.4% | 72.04% | 20M/mL |
| 19 | | 68.2% | 15M/mL |
| 22 | | 67% | 18.6M/mL |
| 25 | | 72.2% | 20.1M/mL |

Batch #2:

Donor ID #: 6302.

Initial viability after liver digestion and single cell hepatocyte isolation: 67.5%. For a total of about 5 billion live isolated hepatocytes (5.5M/mL with a total of 900 mL solution), 600 ml solution (about 3.3 billion cells) was used for the experiment.

Cell viability post 3-wash cycle and ready for transplantation:

71.7% viability for a total of 624 Million live hepatocytes (4.16M/mL in 150 mL solution).

Store in UW overnight for transplantation next day.

76.3% viability for a total of 567 Million live hepatocytes (8.1M/ml in 70 ml solution).

14 tubes at 107 hepatocytes/ml, 2 ml per tube cryopreserved.

69.7% viability for a total of 1.3 billion cells (9.1M/ml in 150 ml solution). Hepatocytes were resuspended at 25M/ml and 50M/ml and tested for viability using 19, 22 and 25 ga EUS needles. Tables 2 and 3 summarizes the viability scores obtained in different groups tested in this experiment. Control represents the solution that was not pushed through any EUS needle but was handled otherwise the same before the post-test viability assessment.

TABLE 2

| | Viability Results of Batch #2 with 25M/mL Solution | | |
| --- | --- | --- | --- |
| EUS Needle | Cell Viability | | Concentration of |
| Gauge | Pre-Test | Post-Test | cells out of needle |
| Control | 69.7% | 64.5% | 16.8M/mL |
| 19 | | 71.6% | 15.4M/mL |
| 22 | | 67.4% | 18.2M/mL |
| 25 | | 70.7% | 13.6M/mL |

TABLE 3

| | Viability Results of Experiment #2 with 50M/mL Solution | | |
| --- | --- | --- | --- |
| EUS Needle | Cell Viability | | Concentration of |
| Gauge | Pre-Test | Post-Test | cells out of needle |
| Control no needle | 69.7% | 73.1% | 43.9M/mL |
| 19 | | 77.3% | 42.9M/mL |
| 22 | | 78.7% | 50.3M/mL |
| 25 | | 77.2% | 40.6M/mL |

Example 2. Portacaval Shunt in Dog as a Model of Liver Failure

This Example describes an exemplary surgical procedure that creates an animal model for studying regeneration medicine for treatment of liver failure.

Figure 4:
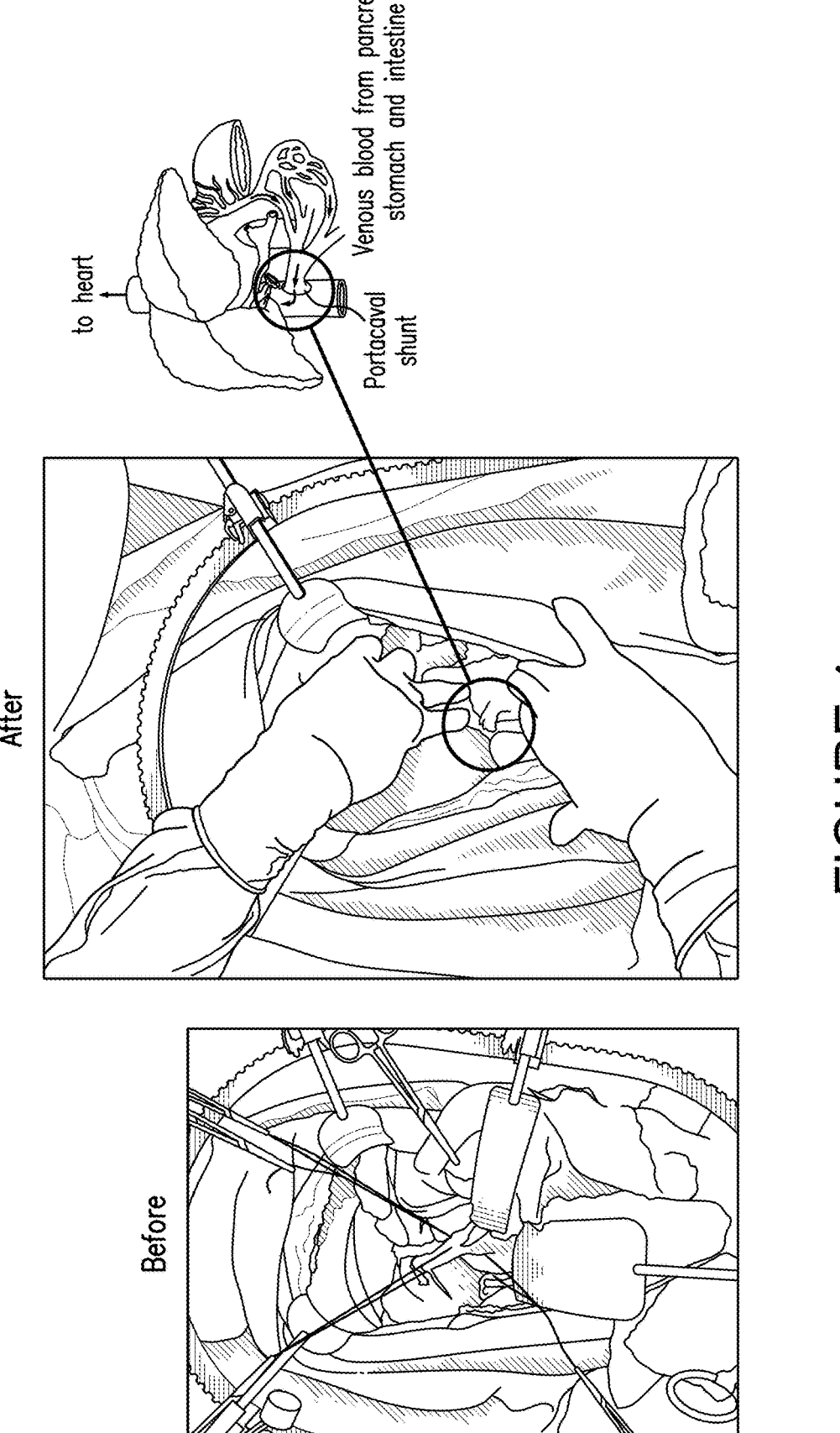
FIG. 4 shows pictures of opened abdominal cavity of an experimental animal before and after a portacaval shunt procedure, as well as a diagram (rightmost) of the portacaval shunt procedure.

As illustrated in FIG. 4, complete portacaval shunt can be performed to shut off major blood flow into the liver, which can induce liver damage. The use of appropriate surgical staplers will allow this procedure to be conducted with almost no blood loss. The mobilization of the main portal vein (PV) within the hepatic hilum by is followed by the isolation of the common bile duct (CBD) and the main hepatic artery (HA). Proximal dissection of the main PV towards the confluence between the superior mesenteric vein (SMV) and the splenic vein (SV) are also performed. Further mobilization of the infra-hepatic inferior vena cava (IVC) with a distal dissection towards the renal veins is conducted. A complete ligation and transection of the main PV before the bifurcation (right and left branches) is conducted with articulated endovascular staples prior to the mobilization of the PV caudally towards the IVC. A complete caudal mobilization of the PV towards the IVC is conducted and an end to side anastomosis between the PV to the IVC (running sutures of 6-0 Prolene) is performed. This step involves partial clamping of the IVC and total clamping of the proximal PV. After full hemostasis was achieved, the abdominal cavity is then closed. The animals were extubated in the OR after full recovery from the general anesthesia.

Example 3. Pre-clinical Study of EUS-Guided Delivery of Hepatocytes for Organogenesis in Lymph Node This Example illustrates treatment of liver failure in a large animal (canine) model by EUS-guided delivery of hepatocytes into periduodenal lymph node (LN).

The pre-clinical experiments in a large animal model (canine) described herein are approved by an IACUC protocol under USDA guidelines and are conducted at a fee-for-service lab at the Allegheny Health Network, Highmark, Pittsburgh, PA In these experiments, hepatocyte transplants are performed in a canine model where liver failure has been induced after a complete portacaval shunt (PCS) has been surgically developed.

Briefly, two groups of animals are tested to confirm that hepatocyte transplantation into the periduodenal lymph nodes (PDLN) induces the generation of new ectopic liver buds (organogenesis) with normal hepatic cytoarchitecture and full functionality. The control group undergoes a complete surgical PCS followed by sham infusion of normal saline into the LN. The study groups undergo the same initial PCS procedure prior to either autologous or allogeneic hepatocyte transplantation into the PDLN through a EUS approach. Both groups receive non-specific immunosuppressive therapy composed of Tacrolimus and Prednisone. Both groups are followed up for 6 months after the initial procedures. The control group animals experience progressive liver failure with 30% mortality over the duration of the study. The study group animals do not show prolonged signs of hepatic failure and have no mortality. These animals show signs of enlargement of the PDLN sites where hepatocytes are initially transplanted. During the end of study necropsy these animals show the development of ectopic hepatic tissue in these PDLN with normal anatomical and histological features. The ectopic livers in the PDLN display clinical and laboratorial evidence of sustainable hepatic function for the duration of the study.

Figure 1B:
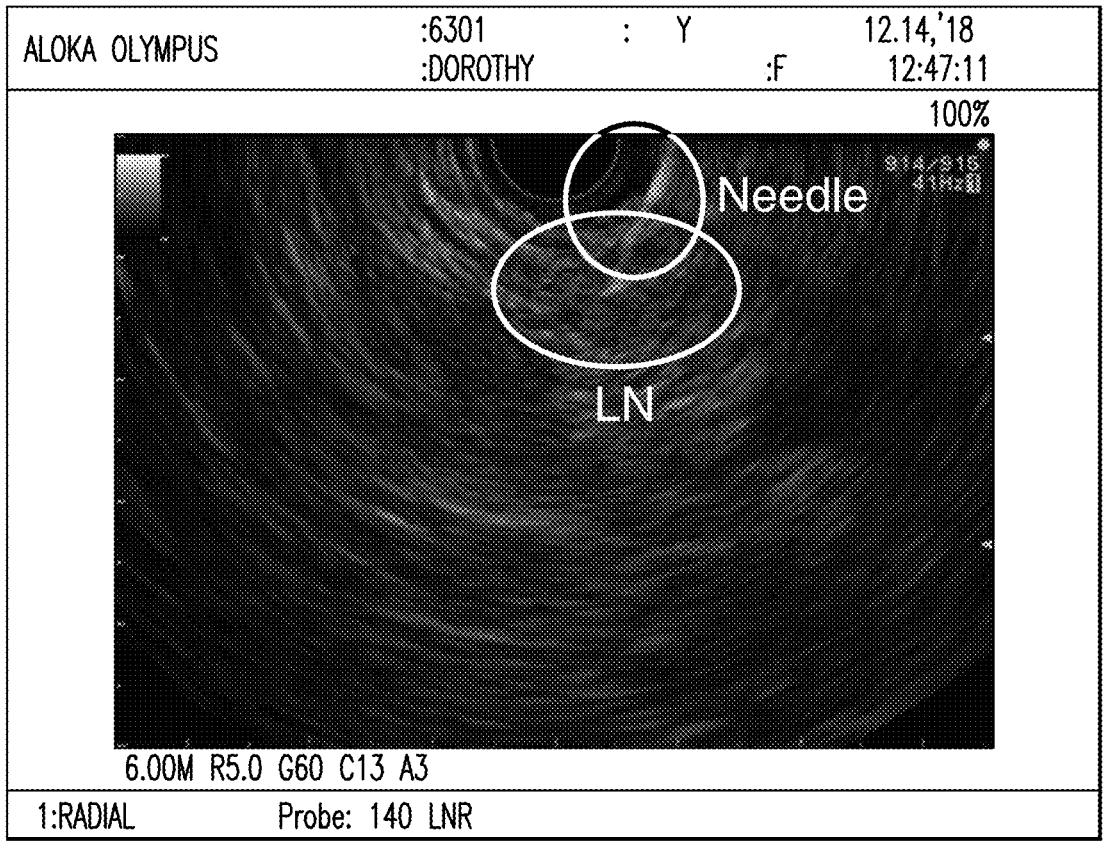
FIG. 1B is a picture of sonography showing the ultrasound image of a Fine Needle Aspiration needle reaching a nearby lymph node (LN).
Figure 2:
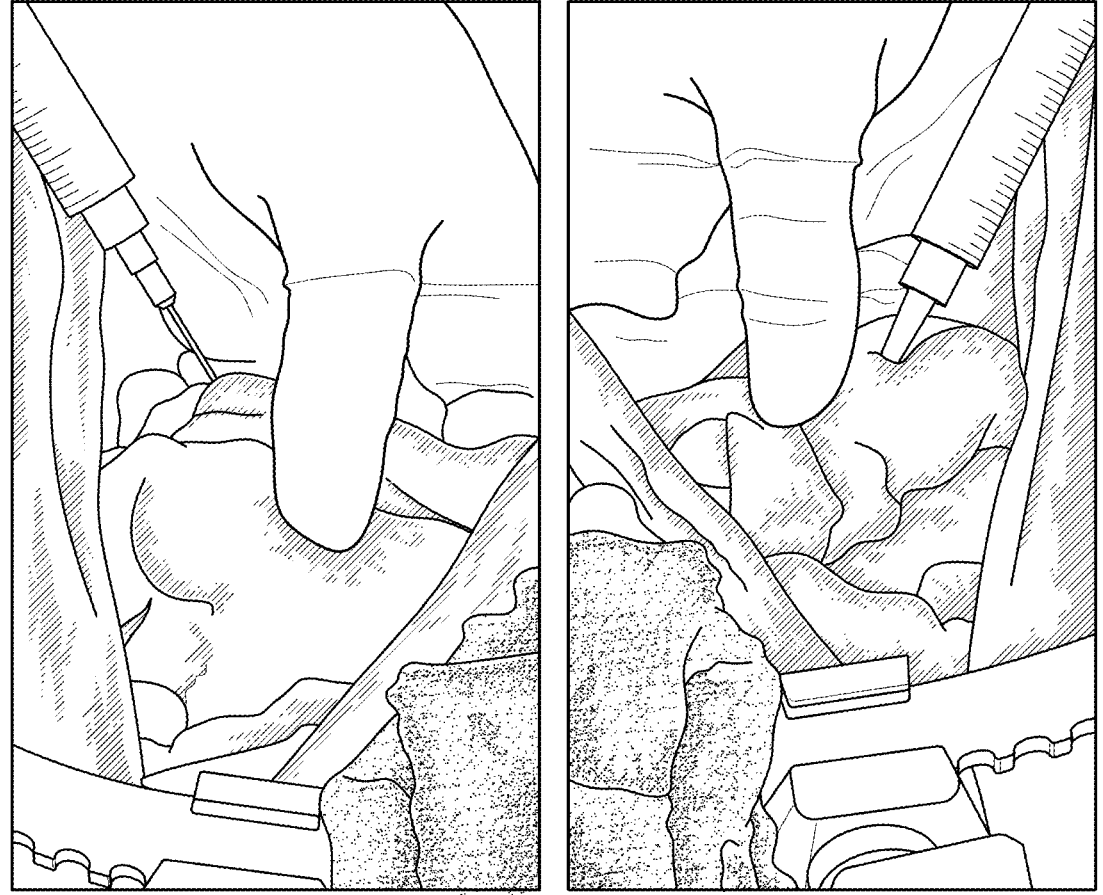
FIG. 2 shows pictures of direct injection of hepatocytes into periduodenal lymph node of an experimental animal conducted by an operative surgeon.
Figure 5:
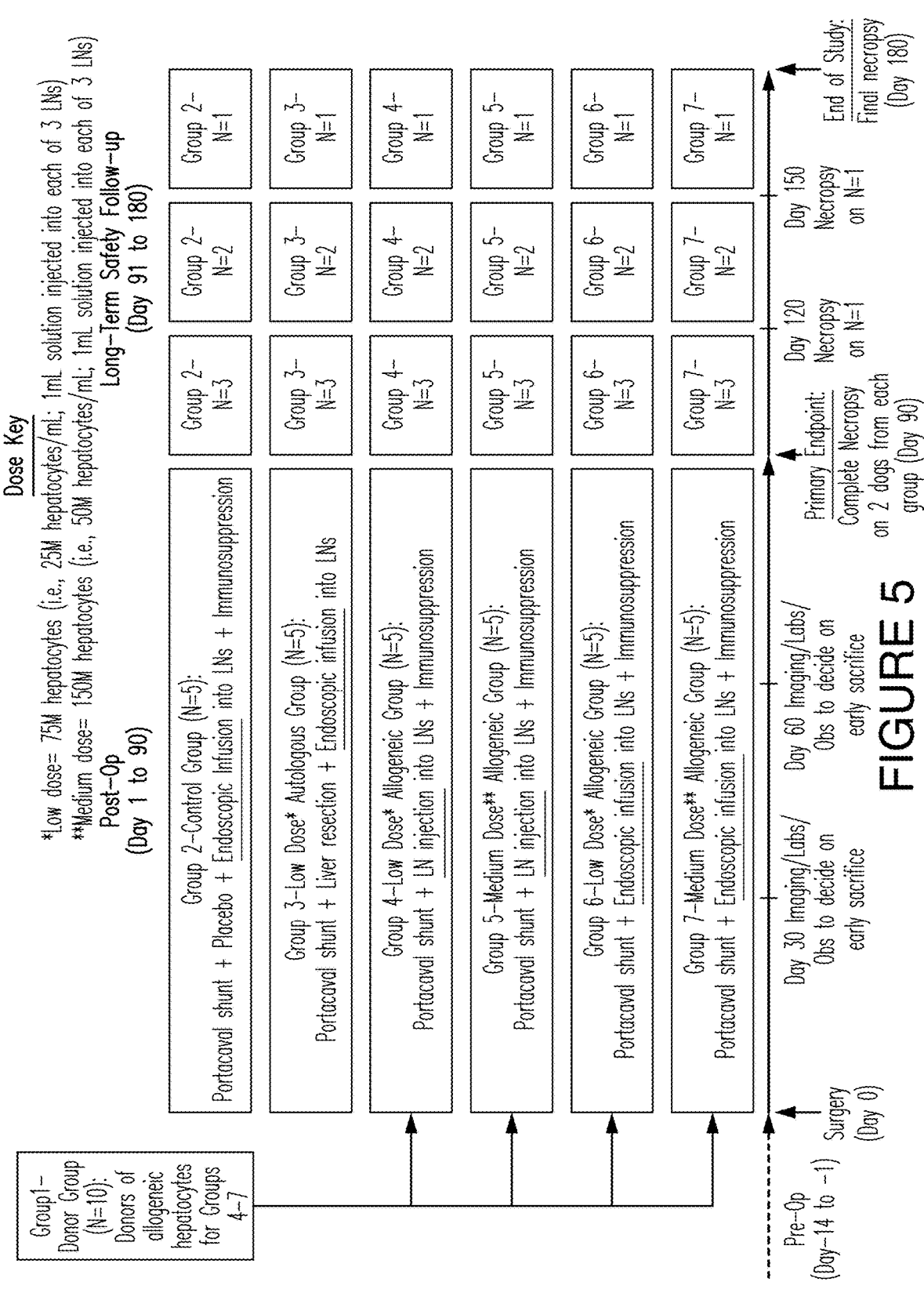
FIG. 5 is a diagram showing the experimental design of a preclinical study according to the present disclosure.

As shown in the study diagram in FIG. 5, Group 1 serves as the donor group for Groups 4-7, which receive allogeneic transplants of hepatocytes (HTs). Group 2 undergoes a PCS procedure along with a placebo infusion (saline) into their LNs. Group 3 is the autologous control group. Groups 4 and 5 receive direct injection of HTs (as shown in FIG. 2) into LNs at low (75M HTs; 25M hepatocytes/mL, with 1 mL of solution injected into each of 3 LNs) or medium dose levels (150M HTs; 50M hepatocytes/mL, with 1 mL of solution injected into each of 3 LNs). Groups 6 and 7 receive their HT transplants through a minimally invasive endoscopic ultrasound (EUS) approach (as shown in FIGS. 1A and 1B), with both the low and medium doses outlined above.

The primary endpoint is at 90 days (N=2 sacrifices from each of Groups 2-7), with additional long-term safety follow-ups from Days 91-180, with interim sacrifices of the study animals at Day 120 (N=1 from each of Groups 2-7), Day 150 (N=1 from each of Groups 2-7) and end of study at Day 180 (N=1 from each of Groups 2-7).

Lymph nodes are harvested from animals sacrificed at each time point, fixed in paraformaldehyde, and embedded in optimal cutting temperature compound or paraffin. Sections are prepared, and stained with Hematoxylin and Eosin (H&E) or Hematoxylin with anti-fumarylacetoacetate-hydrolase (FAH) immunostaining. FAH is highly expressed in hepatocytes and thus can be used to identify hepatocytes. Sections are imaged, and histologically evaluated for the presence of engrafted hepatocytes and the formation of ectopic liver tissue.

Statistical Analyses

The primary endpoint is the size and weight (g) of the lymph nodes with the newly engrafted hepatocytes at 90 days. A full-size liver for a medium-large canine (23.7 kg) weighs approximately 767±48 g, which also serve as estimates for the weight of a fully engrafted ectopic liver and the standard deviation of the liver weights within a treatment group. Four of the six treatment groups receive allogenic hepatocytes in doses of either 75M (low dose) or 150M (medium dose) by direct injection or endoscopic infusion into their lymph nodes. A two-way analysis of covariance (ANCOVA) of the 4 allogenic groups, adjusting for the animal's total weight (kg), is used to test for endpoint differences in the main effects and interaction of dose level and infusion type. Five (5) dogs per treatment group provide 92% power to detect a 77 g difference in the endpoint (0.8 effect size) between the two levels of each main effect, using an F test with $\alpha=0.05$ (2-sided), and 75% power to detect an interaction between dose level and infusion type when the effect size is 0.6. Without wishing to be bound by a particular theory, there can be an underlying linear relationship as well as significant correlation between liver weight and total weight based on previously reported findings (Kam et al., 1987, Sohlenius-Sternbeck, 2006). This is a conservative estimate of the overall power since it does not account for the covariate adjustment.

A one-way ANOVA with the same endpoint and covariate is also used to perform an overall F test for treatment group differences as well as relevant pairwise comparisons between the six groups. The 6 groups include the 4 allogenic groups described above plus a group receiving 75M autologous hepatocytes via endoscopic infusion, and a control group receiving an endoscopic infusion of saline solution. Five (5) dogs per group can provide 100% power to detect at least one difference of 154 g (20% engraftment) against the null hypothesis of equal means using an overall F test with $\alpha=0.05$ (2-sided). This sample size can achieve 90% power to detect a difference of at least 230 g (30% engraftment) for all stepdown tests using the Tukey-Kramer (pairwise) multiple comparison procedure to preserve a 0.05 significance level. These power calculations are derived through PASS 12 (Hintze, 2013).

Surgical and Experimental Methods (I) Line Placements and Animal Support

The right jugular vein is cannulated with a PE catheter and 0.9% NaCl IV supportive fluids are initiated. A paralytic agent is administered and maintained via a syringe pump or bolus therapy throughout the duration of the procedure. A peripheral artery is cannulated with a PE catheter. A double lumen, long term central venous access (superior vena cava) is further placed through a right cervicotomy and direct access to the external right jugular vein. The permanent central line access is inserted and exteriorized at the posterior cervical region after the completion of the abdominal procedure. The electro cardiac register is monitored through electrodes placed on the animal's body surface. Rectal temperature is continuously monitored. Animal support is in accordance with SOP ANI-017 Guidelines for Performing Survival Surgery in USDA Regulated Species and ANI-032 Thermal Regulation of the Anesthetized Patient.

(II) Left Liver Lobe Segmentectomy for Subsequent Hepatocyte Isolation

The animals are prepped and draped in a sterile fashion after being stable under general anesthesia. The abdominal cavity is entered through a mid-line incision. The liver hilum is initially dissected and the left lateral segment (LLS) is isolated. The left portal vein (PV) and the left hepatic artery (HA) are isolated and encircled with a vascular tape. The LLS is excised through a controlled parenchymal transection in combination with the use of articulated endovascular staples. The left lateral segmentectomy results in approximately 20% removal of the total liver volume. Once the hepatic left lateral segment is removed from the operative field, the specimen is processed in a back table (BT) procedure under sterile conditions. The BT involves flushing of the left PV and left HA with cold lactate ringer (LR) to remove all the blood (flushing step), followed by the infusion of Belzer Solution for subsequent hepatic preservation. The hepatic segment is packed in a double plastic bag and placed on an ice cooler for subsequent transportation to the lab where subsequent cell isolation is conducted (to obtain hepatocytes).

(III) Portacaval Shunt

Extended surgical dissection of the hepatic hilum is performed after the completion of the left lateral segmentectomy. The complete portacaval shunt is performed according to the procedure as described in Example 2.

(IV) Hepatocyte Isolation for Transplantation

Liver cells are isolated according to the procedure described in Example 1. The resulting liver cell suspension is filtered and washed. The trypan blue exclusion test is used to ascertain the viability of isolated hepatocytes. In the auto-transplant group, where the animals received their own hepatocytes, the animals remain under general anesthesia for 5 additional hours while the cells are isolated and prepared for subsequent infusion.

(V) Hepatocyte Transplantation through Direct Surgical Infusion

Hepatocyte cell transplantation is conducted by the operative surgeons after samples for quality control (cell viability, cell count, culture and sensitivity) are obtained. Mesenteric and periduodenal lymph nodes receive direct intra parenchymal cell infusions (cell yield from $25 \times 10^6$ to $50 \times 10^6$ viable cells/ml within a small volume (1 to 3 ml) in infusion media) through either a direct surgical approach, or via endoscopic injection (described below), as determined by assigned experimental group. Proper hemostasis is fully achieved after the heterotopic hepatocyte infusion into the lymph nodes. The abdominal cavity is profusely irrigated with antibiotics and antifungal (Neomycin 500 mg/L, Polymyxin 15,000 units/kg/L, Bacitracin 1000 units/kg/L and Amphotericin B 4 mg/kg/L) solutions after meticulous hemostasis is achieved. The abdominal wall is closed in a three-layer fashion and no drains are utilized. A sealing surgical dressing is placed over the skin closure. The animals are properly recovered from the general anesthesia procedure and further extubated in the operative room. The animals are subsequently transferred to a properly equipped animal facility to receive their post-operative care.

(VI) Hepatocyte Transplantation through an Intraluminal Endoscopic Approach

The endoscopic injection is performed in the animal under general anesthesia after the completion of the PCS. A certified biliary-pancreatic endoscopist with extensive experience in EUS conducts these procedures. A linear echoendoscope (Olympus GF-UCT 180) is utilized for these experiments. The scope is introduced through the animal's mouth and advanced to the stomach and the duodenum. The endoscopic ultrasound (EUS) probe assists and guides the localization of the periduodenal lymph nodes (LN). The LN is directly reached through a transgastric and/or transduodenal approach. Once the LN is properly entered with fine needle aspiration (FNA) needles (Boston scientific, ranging from 19 to 25 G needles), the operative surgeon assists the endoscopist to conduct the hepatocyte transplants after the successful needle insertion into the LN through this EUS guided procedure. The previously isolated hepatocytes are kept in a solution containing $25 \times 10^6$ cells/mL or $50 \times 10^6$ cells/mL. The hepatocytes in solution are transplanted directly into the periduodenal LN, using fine needle aspiration (FNA) needle (Boston scientific, ranging from 19 to 25 G needles). Once the surgical procedure is completed the animals are properly recovered from the general anesthesia procedure and further extubated in the operative room. The animals are subsequently transferred to a properly equipped animal facility to receive their postoperative care.

(VII) Recovery and Post-Operative Care

The animals are allowed to recover from anesthesia with appropriate monitoring while resuming spontaneous ventilation. Animals are monitored 24 hours per day for the first 2-3-days post-surgery (longer if indicated) by trained Preclinical Facility Staff, then at least daily for the duration of the study. The postoperative care of the animals is under the direction of the Study Director in consultation with the veterinarians.

The animals are closely and frequently monitored. Each animal is assessed based on the following species-specific criteria for the evaluation and alleviation of pain: Vocalizations, depression, respiration >50% increase (based on 20/min, the average respiration rate in canine). In addition, heart rate is monitored. Temperature is also monitored.

Pain Management and Monitoring

The animals are initially monitored hourly for the following indicators of postsurgical pain and distress, using a pain scoring system which includes but is not limited to: overall level of activity, surgical wound, appetite and attitude towards their diet.

Postoperative pain is treated with the described analgesic administrations based on the following indicators: increase in heart rate of ~10-15%; and respiratory rate increases of ~40%. Pain is managed with the scheduled administration of: buprenorphine or butorphanol and ketoprofen, or other adjunct analgesia determined in consultation with the veterinarians.

All animals receive postoperative buprenorphine (0.01 mg/kg IV q6-8 h) analgesia. This is supplemented with ketoprofen (1-2 mg/kg IV) and butorphanol (0.1 mg/kg IV q6 h) if additional or alternative analgesia is required.

Additional Supportive and Preventive Measures

The animals receive daily IV antibiotics for the 1st week and additional medication during the post-operative period. Postoperative animals receive maintenance IV fluids which are adjusted according to clinical and laboratory parameters.

In addition, throughout the post-op period, gastric motility (ileus, etc.) is monitored.

A central line is placed at the end of the operative procedure. This IV access is cleaned and maintained for the duration of the study, unless there are signs of infection, distress to the animal, or dog-inflicted trauma.

Immunosuppressive (IS) Therapy:

The animals receive Solumedrol (1 g IV) in the operative room prior to hepatocyte transplantation. The IS regimen post-operative are the following:

Prograf (approximately 0.3 mg/kg) Po q 12 hours for the duration of this study—monitored and adjusted accordingly to prevent toxicity.

Prednisone 20 mg po qd×1 week

Prednisone 10 mg po qd×1 week

Prednisone 5 mg po qd for the duration of this study.

Example 4. Pre-clinical Study of EUS-Guided Delivery of Hepatocytes for Organogenesis in Lymph Node This Example illustrates the treatment of liver failure in a large animal (canine) model by EUS-guided delivery of hepatocytes into periduodenal lymph node (LN).

The pre-clinical experiments in a large animal model (canine) described herein were approved by an IACUC protocol under USDA guidelines and were conducted at a fee-for-service lab at the Allegheny Health Network, Highmark, Pittsburgh, PA In these experiments, hepatocyte transplants were performed in a canine model where liver failure has been induced after a complete portacaval shunt (PCS) has been surgically developed.

Briefly, groups of animals were tested to confirm that hepatocyte transplantation into the periduodenal lymph nodes (PDLN) can induce the generation of new ectopic liver buds (organogenesis) with normal hepatic cytoarchitecture and full functionality. The study groups underwent a complete surgical PCS procedure prior to either autologous or allogeneic hepatocyte transplantation into the PDLN through an EUS approach, or via direct injection. All groups received nonspecific immunosuppressive therapy composed of Tacrolimus and Prednisone. The groups were followed up for 150 days after the initial procedures.

Animals received HTs via direct injection into LNs (as shown in FIG. 2) or through a minimally invasive endoscopic ultrasound (EUS) approach (as shown in FIGS. 1A and 1B). The animals received either 75 million HTs (25M hepatocytes/mL, with 1 mL of solution injected into each of 3 LNs), or 150 million HTs (50M hepatocytes/mL, with 1 mL of solution injected into each of 3 LNs).

Animals were sacrificed on day 6, 60, 90, or 150.

Figure 6A:
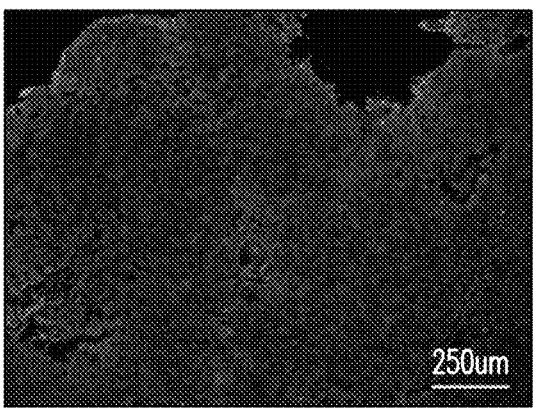
FIG. 6A shows positive staining of CK-18, a marker of hepatocytes, in normal liver tissue.
Figure 6A:
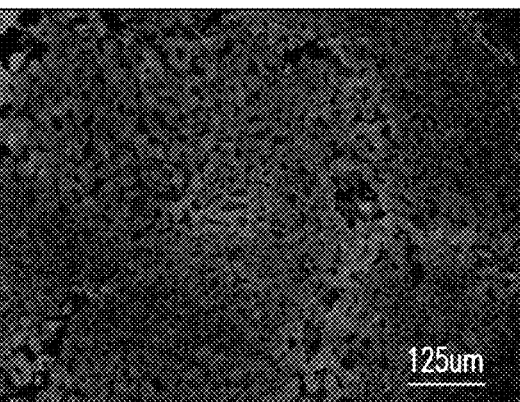
Figure 6B:
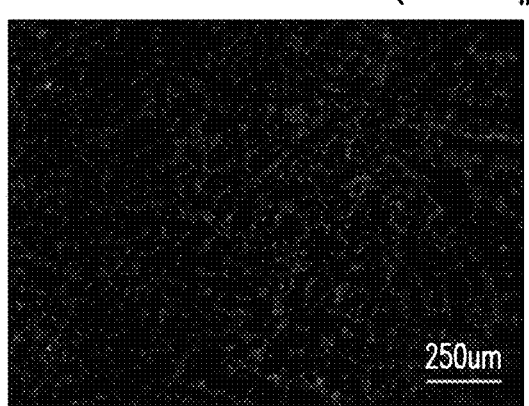
FIG. 6B shows the presence of CK-18 immunostaining signal in lymph nodes 6 days after receiving endoscopic ultrasound (EUS) injection of hepatocytes in a preclinical study.
Figure 6B:
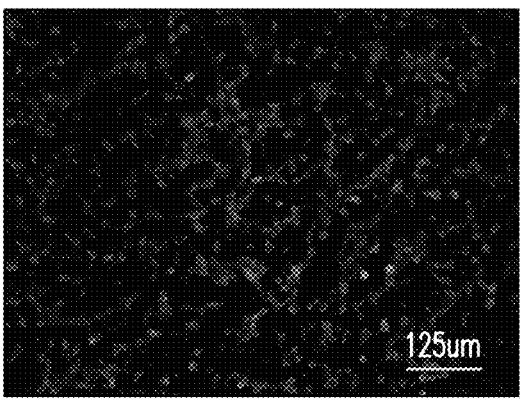
Figure 6C:
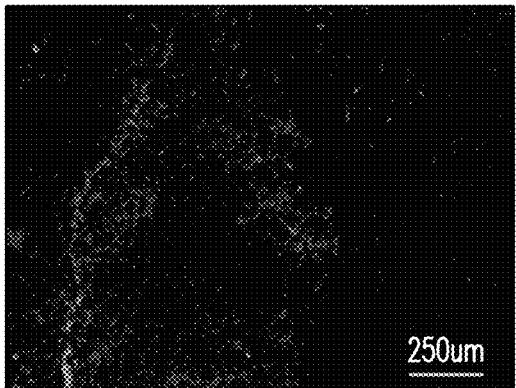
FIG. 6C shows the presence of CK-18 immunostaining signal in lymph nodes 6 days after receiving direct injection of hepatocytes in a preclinical study.
Figure 6C:
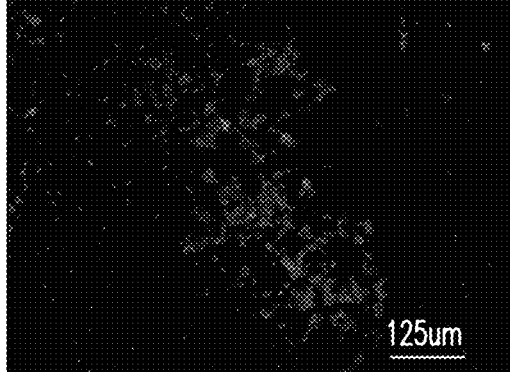

FIG. 6A shows positive staining of CK-18, a marker of hepatocytes, in normal liver tissue, while FIGS. 6B and 6C show the presence of CK-18 immunostained hepatocytes in lymph nodes 6 days after transplantation by EUS and direct injection, respectively. These early results demonstrate the presence of hepatocytes in lymph nodes in both direct injection and EUS injection groups. Primary hepatocytes delivered into lymph nodes via EUS successfully formed liver tissue.

FIGS. 7A-7D show the formation of liver tissue after transplantation of hepatocytes by EUS. Lymph nodes were harvested from animals sacrificed at each time point, fixed in paraformaldehyde, and embedded in paraffin. Sections were prepared, and stained with Hematoxylin and Eosin (H&E) or Hematoxylin with anti-fumarylacetoacetate-hydrolase (FAH) immunostaining. FAH is highly expressed in hepatocytes and thus can be used to identify hepatocytes. Sections were imaged, and histologically evaluated for the presence of engrafted hepatocytes and the formation of ectopic liver tissue.

Figure 7A:
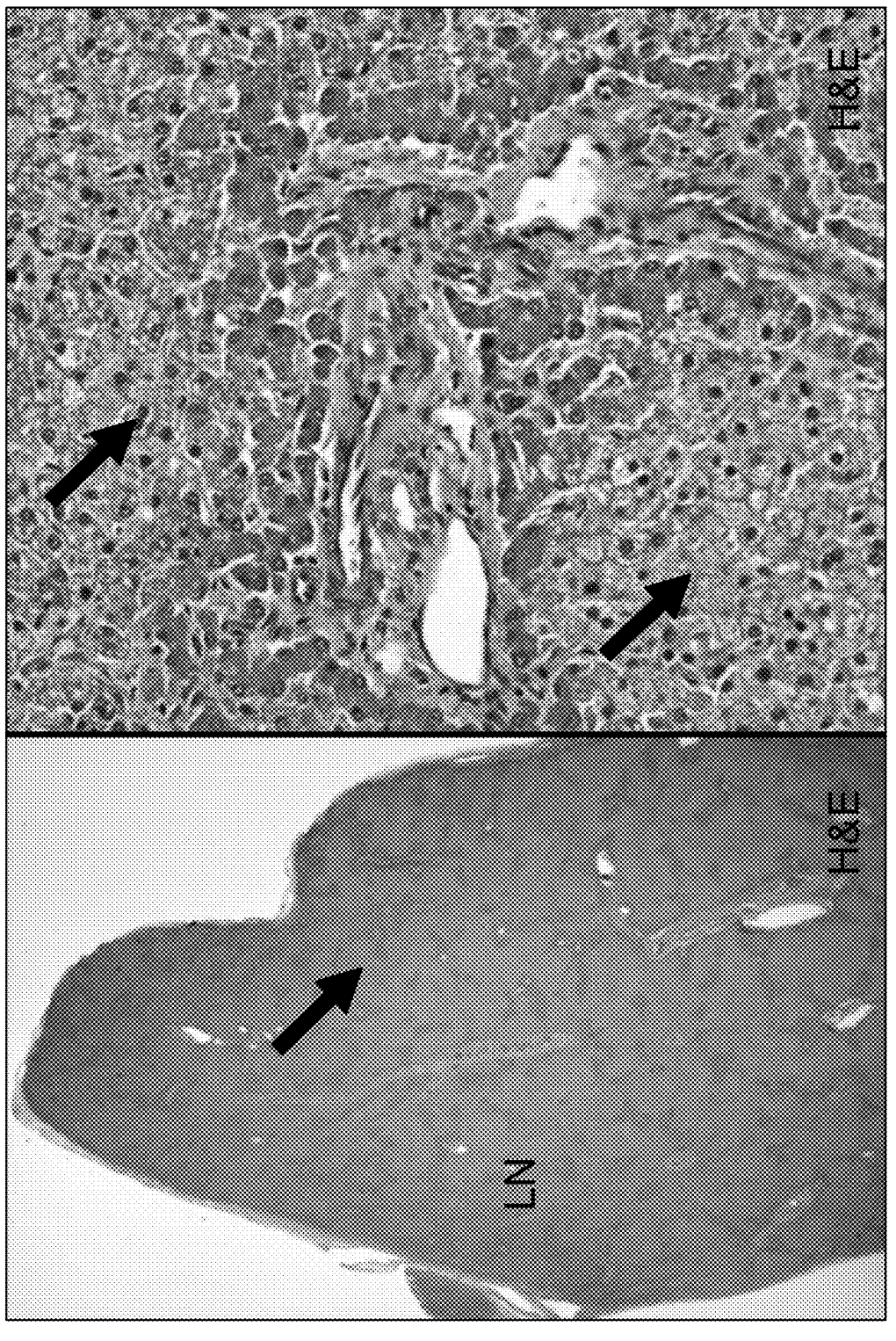
FIG. 7A shows the presence of liver tissue in a lymph node about 90 days after transplantation of autologous hepatocytes into the lymph node by endoscopic ultrasound (EUS) injection.

FIG. 7A shows histology images of a lymph node after transplantation of autologous hepatocytes by EUS. About $25 \times 10^6$ autologous hepatocytes per lymph node were transplanted by EUS, and the lymph node was collected about 90 days after the transplantation. Sections of the lymph node were stained with hematoxylin and eosin (H&E). Higher magnification of H&E staining (right) shows liver tissue (arrows) was formed from the engrafted hepatocytes.

Figure 7B:
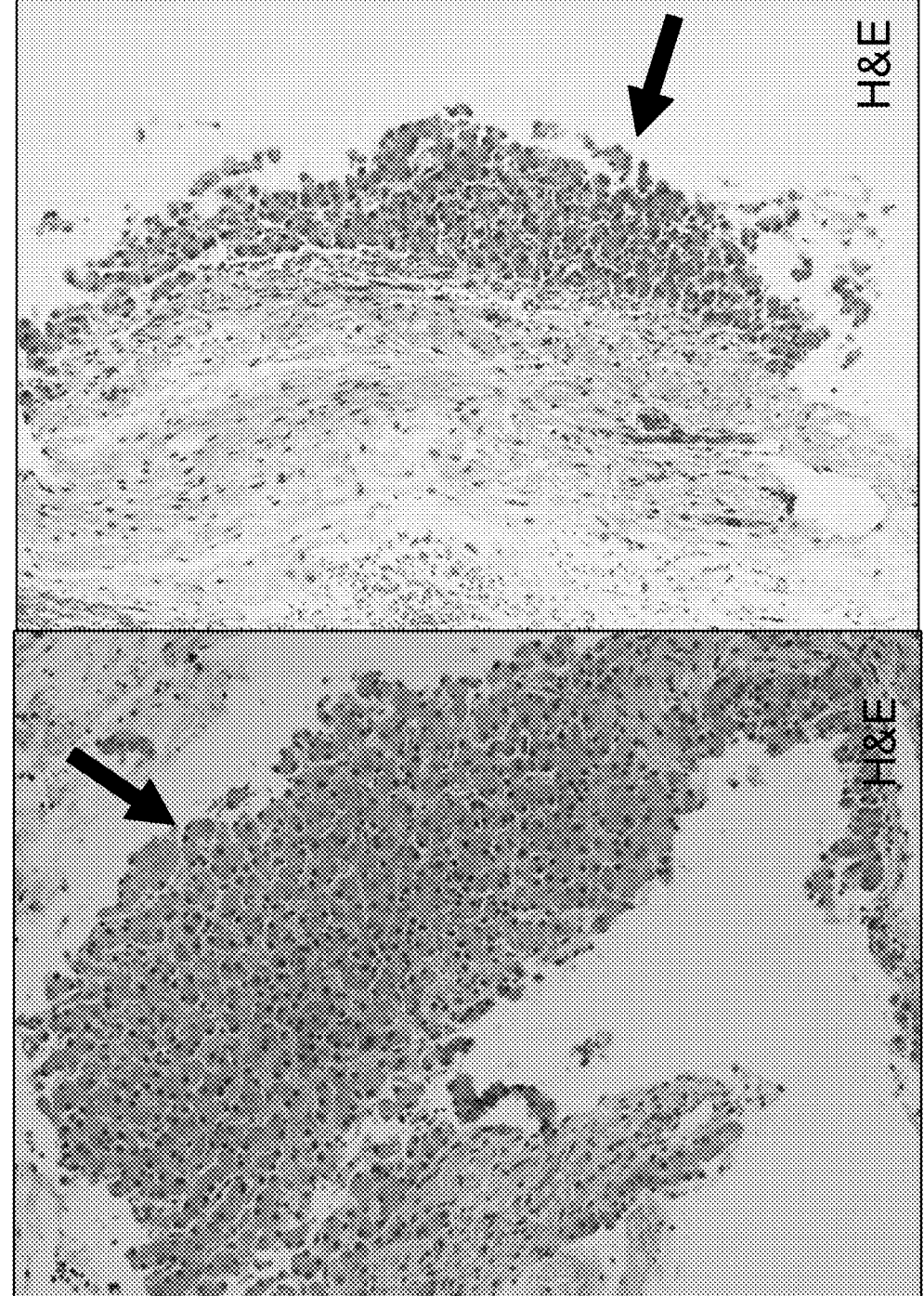
FIG. 7B shows the presence of liver tissue in a lymph node about 90 days after transplantation of allogenic hepatocytes into the lymph node by endoscopic ultrasound (EUS) injection.

FIG. 7B shows histology images of a lymph node after transplantation of allogenic hepatocytes by EUS. About $50 \times 10^6$ allogenic hepatocytes per lymph node were transplanted by EUS, and the lymph node was collected about 90 days after the transplantation. Sections of the lymph node were stained with H&E. Liver tissue (arrows) was formed from the engrafted hepatocytes in various parts of the lymph node.

Figure 7C:
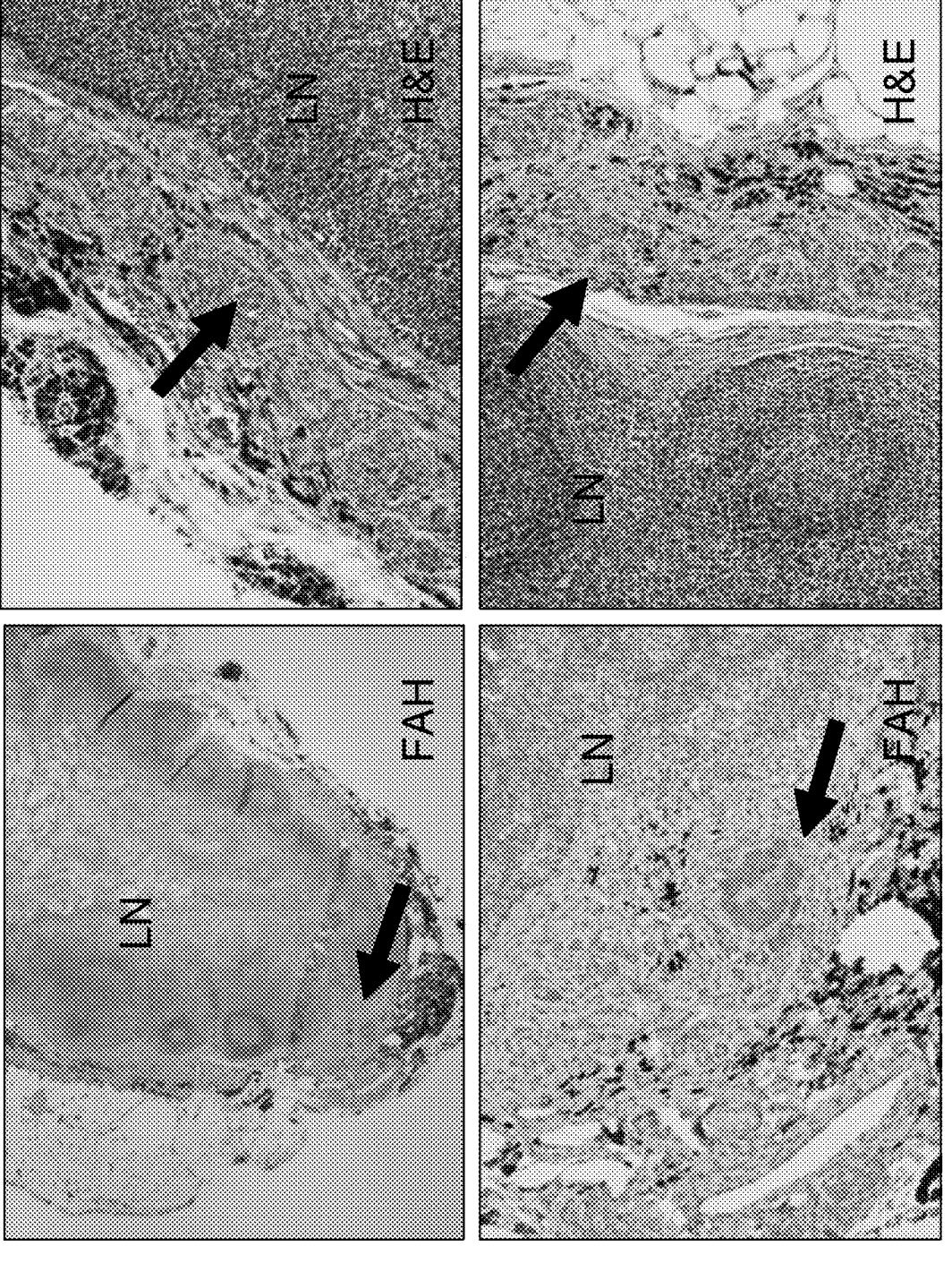
FIG. 7C shows the presence of liver tissue and fumarylacetoacetate-hydrolase (FAH) positive hepatocytes in a lymph node about 60 days after transplantation of autologous hepatocytes into the lymph node by endoscopic ultrasound (EUS) injection.

FIG. 7C shows histology images of a lymph node after transplantation of autologous hepatocytes by EUS. About $50 \times 10^6$ autologous hepatocytes per lymph node were transplanted by EUS, and the lymph node was collected about 60 days after the transplantation. Sections of the lymph node were stained with H&E (right panels) or Hematoxylin with anti-fumarylacetoacetate-hydrolase (FAH) immunostaining (left panels). Liver tissue (arrows) was formed in various parts of the lymph node, and included FAH-positive hepatocytes.

Figure 7D:
FIG. 7D shows the presence of liver tissue and FAH positive hepatocytes in a lymph node about 150 days after transplantation of allogenic hepatocytes into the lymph node by endoscopic ultrasound (EUS) injection.

FIG. 7D shows histology images of a lymph node after transplantation of allogeneic hepatocytes by EUS. About $25 \times 10^6$ allogenic hepatocytes per lymph node were transplanted by EUS, and the lymph node was collected about 150 days after the transplantation. Sections of the lymph node were stained with H&E (right panels) or Hematoxylin with anti-fumarylacetoacetate-hydrolase (FAH) immunostaining (left panels). Liver tissue (arrows) was formed in various parts of the lymph node, and included FAH-positive hepatocytes.

The study group animals did not show prolonged signs of hepatic failure or mortality. These animals showed signs of enlargement of the PDLN sites where hepatocytes were initially transplanted. During the end of study necropsy, these animals showed the development of ectopic hepatic tissue in the PDLN with normal anatomical and histological features. The ectopic livers in the PDLN displayed evidence of sustainable hepatic tissue for the duration of the study.

Surgical and Experimental Methods (I) Line Placements and Animal Support

The right jugular vein was cannulated with a PE catheter, and 0.9% NaCl IV supportive fluids were initiated. A paralytic agent was administered and maintained via a syringe pump or bolus therapy throughout the duration of the procedure. A peripheral artery was cannulated with a PE catheter. A double lumen, long term central venous access (superior vena cava) was further placed through a right cervicotomy and direct access to the external right jugular vein. The permanent central line access was inserted and exteriorized at the posterior cervical region after the completion of the abdominal procedure. The electro cardiac register was monitored through electrodes placed on the animal's body surface. Rectal temperature was continuously monitored. Animal support was in accordance with SOP ANI-017 Guidelines for Performing Survival Surgery in USDA Regulated Species and ANI-032 Thermal Regulation of the Anesthetized Patient.

(II) Left Liver Lobe Segmentectomy for Subsequent Hepatocyte Isolation

The animals were prepped and draped in a sterile fashion after being stable under general anesthesia. The abdominal cavity was entered through a mid-line incision. The liver hilum was initially dissected, and the left lateral segment (LLS) was isolated. The left portal vein (PV) and the left hepatic artery (HA) were isolated and encircled with a vascular tape. The LLS was excised through a controlled parenchymal transection in combination with the use of articulated endovascular staples. The left lateral segmentectomy resulted in approximately 20% removal of the total liver volume. Once the hepatic left lateral segment was removed from the operative field, the specimen was processed in a back table (BT) procedure under sterile conditions. The BT involved the flushing of the left PV and left HA with cold lactate ringer (LR) to remove all the blood (flushing step) followed by the infusion of Belzer Solution for subsequent hepatic preservation. The hepatic segment was packed in a double plastic bag and placed on an ice cooler for subsequent transportation to the lab where subsequent cell isolation is conducted (to obtain hepatocytes).

(III) Portacaval Shunt

Extended surgical dissection of the hepatic hilum was performed after the completion of the left lateral segmentectomy. The complete portacaval shunt was performed according to the procedure, as described in Example 2.

(IV) Hepatocyte Isolation for Transplantation

Liver cells were isolated according to the procedure described in Example 1. The resulting liver cell suspension was filtered and washed. The trypan blue exclusion test was used to ascertain the viability of isolated hepatocytes. In the auto-transplant group, where the animals received their own hepatocytes, the animals remained under general anesthesia for 5 additional hours while the cells were isolated and prepared for subsequent infusion.

(V) Hepatocyte Transplantation through Direct Surgical Infusion

Hepatocyte cell transplantation was conducted by the operative surgeons after samples for quality control (cell viability, cell count, culture, and sensitivity) were obtained. Mesenteric and periduodenal lymph nodes received direct intra parenchymal cell infusions (cell yield from $25 \times 10^6$ to $50 \times 10^6$ viable cells/ml within a small volume (1 to 3 ml) in infusion media) through either a direct surgical approach or via endoscopic injection (described below), as determined by assigned experimental group. Proper hemostasis was fully achieved after the heterotopic hepatocyte infusion into the lymph nodes. The abdominal cavity was profusely irrigated with antibiotics and antifungal (Neomycin 500 mg/L, Polymyxin 15,000 units/kg/L, Bacitracin 1000 units/kg/L, and Amphotericin B 4 mg/kg/L) solutions after meticulous hemostasis was achieved. The abdominal wall was closed in a three-layer fashion, and no drains was utilized. A sealing surgical dressing was placed over the skin closure. The animals were properly recovered from the general anesthesia procedure and further extubated in the operative room. The animals were subsequently transferred to a properly equipped animal facility to receive their post-operative care.

(VI) Hepatocyte Transplantation through an Intraluminal Endoscopic Approach (EUS)

The endoscopic injection was performed in the animal under general anesthesia after the completion of the PCS. A certified biliary-pancreatic endoscopist with extensive experience in EUS conducted these procedures. A linear echoendoscope (Olympus GF-UCT 180) was utilized for these experiments. The scope was introduced through the animal's mouth and advanced to the stomach and the duodenum. The endoscopic ultrasound probe (EUS) probe assisted and guided the localization of the periduodenal lymph nodes (LN). The LN was directly reached through a transgastric and/or transduodenal approach. Once the LN was properly entered with fine needle aspiration (FNA) needles (Boston scientific, ranging from 19 to 25 G needles), the operative surgeon assisted the endoscopist to conduct the hepatocyte transplants after the successful needle insertion into the LN through this EUS guided procedure. The previously isolated hepatocytes were kept in a solution containing $25 \times 10^6$ or $50 \times 10^6$ cells/mL. The hepatocytes in solution were transplanted directly into the periduodenal LN, using fine needle aspiration (FNA) needle (Boston scientific, ranging from 19 to 25 G needles). Once the surgical procedure was completed, the animals were properly recovered from the general anesthesia procedure and further extubated in the operative room. The animals were subsequently transferred to a properly equipped animal facility to receive their postoperative care.

(VII) Recovery and Post-Operative Care

The animals were allowed to recover from anesthesia with appropriate monitoring while resuming spontaneous ventilation. Animals were monitored 24 hours per day for the first 2-3-days post-surgery (longer if indicated) by trained Preclinical Facility Staff, then at least daily for the duration of the study. The postoperative care of the animals was under the direction of the Study Director in consultation with the veterinarians.

The animals were closely and frequently monitored. Each animal was assessed based on the following species-specific criteria for the evaluation and alleviation of pain: Vocalizations, depression, respiration >50% increase (based on 20/min, the average respiration rate in canine). In addition, heart rate was monitored. The temperature was also monitored.

Pain Management and Monitoring

The animals were initially monitored hourly for the following indicators of postsurgical pain and distress, using a pain scoring system which includes but is not limited to: overall level of activity, surgical wound, appetite, and attitude towards their diet.

Postoperative pain was treated with the described analgesic administrations based on the following indicators: increase in heart rate of ~10-15%; and respiratory rate increases of ~40%. Pain was managed with the scheduled administration of: buprenorphine or butorphanol and ketoprofen, or other adjunct analgesia determined in consultation with the veterinarians.

All animals received postoperative buprenorphine (0.01 mg/kg IV q6-8 h) analgesia. This was supplemented with ketoprofen (1-2 mg/kg IV) and butorphanol (0.1 mg/kg IV q6 h) if additional or alternative analgesia is required.

Additional Supportive and Preventive Measures

The animals received daily IV antibiotics for the 1st week and additional medication during the post-operative period. Postoperative animals received maintenance IV fluids, which was be adjusted according to clinical and laboratory parameters.

In addition, throughout the post-op period, gastric motility (ileus, etc.) was monitored.

A central line was placed at the end of the operative procedure. This IV access was cleaned and maintained for the duration of the study unless there are signs of infection, distress to the animal, or dog-inflicted trauma.

Immunosuppressive (IS) Therapy:

The animals received Solumedrol (1g IV) in the operative room prior to hepatocyte transplantation. The IS regimen post-operative are the following:

Prograf (approximately 0.3 mg/kg) Po q 12 hours for the duration of this study—monitored and adjusted accordingly to prevent toxicity.

Prednisone 20 mg po qd×1 week

Prednisone 10 mg po qd×1 week

Prednisone 5 mg po qd for the duration of this study.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the present disclosure may be employed in practicing the present disclosure. It is intended that the following claims define the scope of the present disclosure and that methods and structures within the scope of these claims and their equivalents be covered thereby.

Various patents, patent applications, publications, product descriptions, protocols, and sequence accession numbers are cited throughout this application, the inventions of which are incorporated herein by reference in their entireties for all purposes.

What is claimed is:

1. A minimally invasive method of delivering one or more cells to a lymph node of a subject to produce an ectopic tissue, comprising:

(a) advancing an endoscope through an endoluminal approach into a gastrointestinal, respiratory, or urinary tract of the subject, (b) utilizing a transluminal approach to insert a needle attached to the endoscope through a visceral wall into the lymph node of the subject, and (c) delivering the one or more cells into the lymph node via the needle, wherein the one or more cells comprise at least 10 million cells and the lymph node is one lymph node, thereby producing the ectopic tissue in the lymph node.

2. The method of claim 1, wherein the lymph node is in an abdominal cavity, thoracic cavity, mediastinal region, or retroperitoneal region of the subject.

3. The method of claim 1, wherein the advancing the endoscope, the inserting the needle or both are performed with aid of ultrasound imaging of the lymph node.

4. The method of claim 3, wherein the endoscope comprises an ultrasound probe configured to detect the lymph node.

5. The method of claim 1, wherein the advancing the endoscope, the utilizing the transluminal approach to insert the needle, or both, are performed with aid of radiological imaging, and wherein the radiological imaging comprises dynamic radiological imaging, computed tomography (CT), magnetic resonance imaging (MRI), or a combination thereof.

6. The method of claim 1, wherein the one or more cells are selected from the group consisting of hepatocytes, pancreatic cells or islets, kidney cells or kidney tissue fragments, thymic cells or thymus tissue fragments, and lung cells or lung tissue fragments.

7. The method of claim 1, further comprising isolating the one or more cells from a living donor tissue, or recovering the one or more cells from cryopreservation prior to the delivering.

8. The method of claim 1, wherein the lymph node is in an abdominal cavity of the subject.

9. The method of claim 1, further comprising administering an immunosuppressant to the subject to reduce immune rejection of the one or more cells.

10. The method of claim 1, wherein the at least 10 million cells comprise an average diameter of at least 20 μm.

11. The method of claim 1, wherein the delivering comprises delivering a population of cells that comprise the one or more cells, and wherein the delivering leads to a less than 20% reduction in viability of the population of cells.

12. The method claim 1, wherein an inner diameter of the needle is no greater than 700 μm.

13. The method of claim 1, wherein the method treats a liver disease or condition, a renal disease or condition, an endocrine pancreatic disease or condition that leads to reduction or absence of insulin secretion, a lung disease or condition, or an age-related immune system malfunction in the subject.

14. The method of claim 1, wherein the lymph node is in proximity to the gastrointestinal tract, and (a) comprises advancing the endoscope through the endoluminal approach into the gastrointestinal tract.

15. The method of claim 14, wherein the one or more cells comprise one or more hepatocytes.

16. The method of claim 1, wherein the lymph node is selected from the group consisting of a periduodenal lymph node, a perigastric lymph node, a peripancreatic lymph node, a mesenteric lymph node, an ileocolic lymph node, a mesocolic lymph node, a gastric lymph node, a hepatic splenic lymph node, a splenic hilar lymph node, a paraoesophageal lymph node, a paracardial lymph node, a paraaortic lymph node, a retroaortic lymph node, a lateral aortic lymph node, a preaortic lymph node, a lesser curve lymph node, a common hepatic lymph node, a splenic artery lymph node, a coeliac axis lymph node, an iliac lymph node, a retroperitoneal lymph node, and combinations thereof.

17. The method of claim 1, wherein the lymph node is in proximity to the respiratory tract, and (a) comprises advancing the endoscope through the endoluminal approach into the respiratory tract.

18. The method of claim 17, wherein the lymph node comprises a lymph node in a mediastinal region of the subject.

19. The method of claim 17, wherein the lymph node comprises a parasternal lymph node, an intercostal lymph node, a superior diaphragmatic lymph node, a superior tracheobronchial lymph node, an inferior tracheobronchial lymph node, a bronchopulmonary lymph node, a paratracheal lymph node, or an intrapulmonary lymph node.

20. The method of claim 1, wherein the lymph node is in proximity to the urinary tract, and (a) comprises advancing the endoscope through the endoluminal approach into the urinary tract.

21. The method of claim 20, wherein the lymph node comprises a lymph node in a retroperitoneal region of the subject.

22. The method of claim 20, wherein the lymph node comprises an external iliac lymph node, an internal iliac lymph node, a caval lumbar lymph node, an aortic lumbar lymph node, a superficial inguinal lymph node, a profound inguinal lymph node, an interaortocaval peri-bladder lymph node, an obturator peri-bladder lymph node, or a pre-sacral peri-bladder lymph node.

23. The method of claim 1, wherein the ectopic tissue is formed within about 200 days after the delivering the one of more cells into the lymph node.

24. The method of claim 1, wherein the one or more cells are allogeneic to the subject.

25. The method of claim 1, wherein:

(i) the one or more cells are allogeneic to the subject;

(ii) the one or more cells comprise hepatocytes and the ectopic tissue is ectopic liver tissue;

(iii) an inner diameter of the needle is at most 700 µm;

(iv) the lymph node is in proximity to the gastrointestinal tract, (v) (a) comprises advancing the endoscope through the endoluminal approach into the gastrointestinal tract;

(vi) the advancing the endoscope, the utilizing a transluminal approach to insert the needle, or both, are performed with aid of ultrasound imaging of the lymph node, wherein the endoscope comprises an ultrasound probe configured to detect the lymph node;

(vii) (c) comprises delivering a population of cells that comprise the one or more cells into the lymph node, wherein the delivering leads to a less than 20% reduction in viability of the population of cells; and (viii) the method treats end stage liver disease in the subject.

26. The method of claim 25, wherein the lymph node is a periduodenal lymph node.

27. The method of claim 1, wherein the lymph node is a coeliac axis lymph node, gastric lymph node, hepatic lymph node, splenic lymph node, pyloric lymph node, or superior mesenteric lymph node.

28. The method of claim 1, wherein the lymph node is a perigastric lymph node, a peripancreatic lymph node, a mesenteric lymph node, a hepatic splenic lymph node, a splenic hilar lymph node, a paraoesophageal lymph node, a paraaortic lymph node, a retroaortic lymph node, a lateral aortic lymph node, a preaortic lymph node, a lesser curve lymph node, a common hepatic lymph node, a splenic artery lymph node, a superior mesenteric lymph node, a left lumbar lymph node, a cystic lymph node, super pyloric lymph node, a sub pyloric lymph node, a retro pyloric lymph node, a superior pancreatic lymph node, an inferior lymph node, a superior pancreaticoduodenal lymph node, or an inferior pancreaticoduodenal lymph node.

29. The method of claim 1, wherein the method further comprises delivering at least 10 million cells into a second lymph node.

30. The method of claim 29, wherein the method further comprises delivering at least 10 million cells into a third lymph node.

31. The method of claim 30, wherein the method further comprises (i) delivering at least 10 million cells into a fourth lymph node, and (ii) delivering at least 10 million cells into a fifth lymph.

32. The method of claim 1, wherein the method further comprises utilizing the transluminal approach to insert the needle attached to the endoscope through a visceral wall into a second lymph node of the subject, and delivering at least 10 million cells into the second lymph node via the needle.

33. The method of claim 32, wherein the method further comprises utilizing the transluminal approach to insert the needle attached to the endoscope through a visceral wall into a third lymph node of the subject, and delivering at least 10 million cells into the third lymph node via the needle.

34. The method of claim 33, wherein the method further comprises (i) utilizing the transluminal approach to insert the needle attached to the endoscope through a visceral wall into a fourth lymph node of the subject, and delivering at least 10 million cells into the fourth lymph node via the needle; and (ii) utilizing the transluminal approach to insert the needle attached to the endoscope through a visceral wall into a fifth lymph node of the subject, and delivering at least 10 million cells into the fifth lymph node via the needle.

35. A method of treating a liver disease in a subject in need thereof, comprising (a) advancing an endoscope through an endoluminal approach into a gastrointestinal, respiratory, or urinary tract of the subject, (b) utilizing a transluminal approach to insert a needle attached to the endoscope through a visceral wall into a lymph node of the subject with aid of ultrasound imaging, and (c) delivering the one or more cells into the lymph node via the needle, wherein the one or more cells comprise at least 10 million cells and the lymph node is one lymph node, thereby producing an ectopic liver tissue in the lymph node and treating the liver disease.

36. The method of claim 35, wherein the method treats end stage liver disease in the subject.

37. The method of claim 35, wherein (a) comprises advancing the endoscope through the endoluminal approach into the gastrointestinal tract of the subject, and wherein the lymph node is in proximity to the gastrointestinal tract.

* * * * *